US012048848B2

(12) United States Patent
Li et al.

(10) Patent No.: US 12,048,848 B2
(45) Date of Patent: *Jul. 30, 2024

(54) LEAD INTEGRITY AND CLOSED-LOOP ALGORITHM DIAGNOSTIC

(71) Applicant: Medtronic, Inc., Minneapolis, MN (US)

(72) Inventors: Jiashu Li, Mounds View, MN (US); Duane L. Bourget, Andover, MN (US); Kristin N. Hageman, Dayton, MN (US); Hank Bink, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,348

(22) Filed: Apr. 27, 2023

(65) Prior Publication Data
US 2023/0302281 A1  Sep. 28, 2023

Related U.S. Application Data

(63) Continuation of application No. 16/948,748, filed on Sep. 30, 2020, now Pat. No. 11,648,402.

(51) Int. Cl.
*A61N 1/36* (2006.01)
*A61N 1/08* (2006.01)

(52) U.S. Cl.
CPC ........... *A61N 1/36139* (2013.01); *A61N 1/08* (2013.01); *A61N 1/3614* (2017.08); *A61N 2001/083* (2013.01)

(58) Field of Classification Search
CPC .... A61N 1/36139; A61N 1/3614; A61N 1/08; A61N 1/0551; A61N 1/36062;
(Continued)

(56) References Cited

U.S. PATENT DOCUMENTS 7,574,259 B1   8/2009   Pei et al.
8,217,523 B2   7/2012   Brown et al.
(Continued)

FOREIGN PATENT DOCUMENTS

CN      108310649 A     7/2018
WO    2018080754 A1     5/2018
(Continued)

OTHER PUBLICATIONS

"Energy Harvesting from Moving Organs to Power Medical Implants (Video)," retrieved from https://www.medgadget.com/2014/01/energy-harvesting-from-moving-organs.html, on Mar. 30, 2020, 3 pp.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

In one example, the disclosure describes a method comprising receiving, by processing circuitry, information indicative of one or more evoked compound action potential (ECAP) signals. The one or more ECAP signals are sensed by at least one electrode carried by a medical lead. The processing circuitry determining that at least one characteristic value of the one or more ECAP signals is outside of an expected range. Responsive to determining that the at least one characteristic value of the one or more ECAP signals is outside of the expected range, the processing circuitry performs a lead integrity test for the medical lead.

20 Claims, 10 Drawing Sheets

(58) Field of Classification Search
CPC . A61N 2001/083; A61B 5/1118; A61B 5/686; A61B 5/0031; A61B 5/1116; A61B 5/4836; A61B 5/246; A61B 5/293; A61B 5/388; A61B 2562/0219
See application file for complete search history.

(56) References Cited

U.S. PATENT DOCUMENTS

| | | |
|---|---|---|
| 9,026,212 B2 | 5/2015 | Imran |
| 9,847,739 B2 | 12/2017 | Deterre et al. |
| 9,872,757 B2 | 1/2018 | Kelly et al. |
| 9,884,180 B1 | 2/2018 | Ho et al. |
| 10,044,218 B2 | 8/2018 | Tiefnig |
| 10,581,344 B2 | 3/2020 | Cottone et al. |
| 11,547,860 B2 | 1/2023 | Hareland et al. |
| 11,559,689 B2 | 1/2023 | Hareland |
| 11,648,402 B2 | 5/2023 | Li et al. |
| 2006/0093785 A1 | 5/2006 | Hickle |
| 2008/0114219 A1 | 5/2008 | Zhang et al. |
| 2009/0299421 A1 | 12/2009 | Sawchuk |
| 2010/0049270 A1 | 2/2010 | Pastore et al. |
| 2010/0114221 A1 | 5/2010 | Krause et al. |
| 2011/0304240 A1 | 12/2011 | Meitav et al. |
| 2011/0307032 A1 | 12/2011 | Goetz et al. |
| 2013/0103106 A1 | 4/2013 | Schotzko et al. |
| 2015/0012068 A1 | 1/2015 | Bradley et al. |
| 2015/0112408 A1 | 4/2015 | Kals |
| 2015/0151132 A1 | 6/2015 | Pei et al. |
| 2016/0030749 A1 | 2/2016 | Carcieri et al. |
| 2016/0361551 A1 | 12/2016 | Kaula et al. |
| 2017/0069823 A1 | 3/2017 | Karpelson |
| 2018/0126169 A1 | 5/2018 | Hou et al. |
| 2019/0000332 A1 | 1/2019 | Li et al. |
| 2019/0038902 A1 | 2/2019 | Kaemmerer et al. |
| 2019/0091479 A1 | 3/2019 | Bonnet |
| 2019/0099601 A1 | 4/2019 | Torgerson |
| 2019/0151666 A1 | 5/2019 | Bonnet |
| 2019/0350169 A1 | 11/2019 | Weinrauch et al. |
| 2019/0381325 A1 | 12/2019 | Regnier et al. |
| 2019/0388692 A1 | 12/2019 | Dinsmoor et al. |
| 2019/0393406 A1 | 12/2019 | Chen et al. |
| 2020/0179688 A1 | 6/2020 | Su |
| 2020/0406041 A1 | 12/2020 | Cao et al. |
| 2021/0268296 A1 | 9/2021 | Flakne et al. |
| 2021/0379383 A1 | 12/2021 | Single et al. |

FOREIGN PATENT DOCUMENTS

| | | |
|---|---|---|
| WO | 2019246579 A1 | 12/2019 |
| WO | 2019246582 A1 | 12/2019 |

OTHER PUBLICATIONS

Baranth et al., "New Pacemaker Harvests Energy from the Heart," Scientific American, May 28, 2019, 4 pp.

Cadei et al., "Kinetic and Thermal Energy Harvesters for Implantable Medical Devices and Biomedical Autonomous Sensors," Measurement Science and Technology, vol. 25, Nov. 13, 2013, 14 pp.

Hannan et al., "Energy Harvesting for the Implantable Biomedical Devices: Issues and Challenges," BioMedical Engineering OnLine, vol. 13, No. 79, Jun. 20, 2014, 23 pp.

International Search Report and Written Opinion of International Application No. PCT/US2021/052123, dated Feb. 4, 2022, 9 pp.

Madhusoodanan et al., "Inner Workings: Self-Powered Biomedical Devices Tap into the Body's Movements," PNAS, vol. 116, No. 36, Sep. 3, 2019, 3 pp.

Niu et al., "A Universal Self-Charging System Driven by Random Biomechanical Energy for Sustainable Operation of Mobile Electronics," Nature Communications, Dec. 11, 2015, 8 pp.

Ouyang et al., "Symbiotic Cardiac Pacemaker," Nature Communications, No. 10, vol. 1, Apr. 2019, 11 pp.

Prosecution History from U.S. Appl. No. 16/948,748, now issued U.S. Pat. No. 11,648,402, dated Jun. 1, 2022 through Feb. 8, 2023, 99 pp.

U.S. Appl. No. 17/100,455, filed Nov. 20, 2020, naming inventors Pulliam et al.

U.S. Appl. No. 62/986,458, filed Mar. 6, 2020, naming inventor Li.

LEAD INTEGRITY AND CLOSED-LOOP ALGORITHM DIAGNOSTIC

This application is a continuation of U.S. patent application Ser. No. 16/948,748, filed Sep. 30, 2020, the entire contents of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure is directed to devices, systems, and techniques for controlling electrical stimulation therapy based on sensing artifacts of at least one of stimulation signals or evoked compound action potentials (ECAPs). A medical device (e.g., an implantable medical device) may deliver one or more stimulation signals (e.g., one or more pulses) to the patient via one or more leads, and the medical device may sense signals which may include respective ECAPs elicited by the pulses. The medical device may also sense ECAP signals elicited by a delivered pulse if the delivered pulse causes a sufficient number of nerve fibers to depolarize.

Examples of the present disclosure generally relate to identifying issues that may occur during closed-loop stimulation, where the system employs ECAP signals in a closed-loop system to adjust one or more stimulation parameters that define subsequent stimulation pulses in electrical stimulation therapy. The issues may relate to medical lead integrity issues and/or noise interference (e.g., electromagnetic interference EMI) that may cause problems with properly detecting and/or recording ECAPs, which in turn affect the closed-loop stimulation ability to properly administer a patient's therapy. Therefore, the system may determine whether or not the detected signals are representative of expected ECAP signals and, if not expected, initiate a lead integrity test to identify the cause of the unexpected signals.

In one example, the disclosure relates to a method comprising receiving, by processing circuitry, information indicative of one or more evoked compound action potential (ECAP) signals. The one or more ECAP signals are sensed by at least one electrode carried by a medical lead. The processing circuitry determining that at least one characteristic value of the one or more ECAP signals is outside of an expected range. Responsive to determining that the at least one characteristic value of the one or more ECAP signals is outside of the expected range, the processing circuitry performs a lead integrity test for the medical lead.

In some examples, the disclosure relates to a medical device comprising stimulation generation circuitry configured to deliver a first stimulation pulse to a patient. Sensing circuitry of the medical device is configured to sense information indicative of one or more evoked compound action potential (ECAP) signals, where the sensing circuitry comprises at least one electrode carried by a medical lead. Processing circuitry of the medical device is configured to receive information indicative of the one or more ECAP signals sensed by the at least one electrode carried by the medical lead. The processing circuitry determines that at least one characteristic value of the one or more ECAP signals is outside of an expected range. Responsive to determining that the at least one characteristic value of the one or more ECAP signals is outside of the expected range, the processing circuitry performs a lead integrity test for the medical lead.

In some examples, a computer-readable storage medium comprises instructions that, when executed, cause processing circuitry to receive information indicative of one or more evoked compound action potential (ECAP) signals. The one or more ECAP signals are sensed by at least one electrode carried by a medical lead. The processing circuitry determines that at least one characteristic value of the one or more ECAP signals is outside of an expected range. Based on the determination that the at least one characteristic value of the one or more ECAP signals is outside of the expected range, the processing circuitry performs a lead integrity test for the medical lead.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
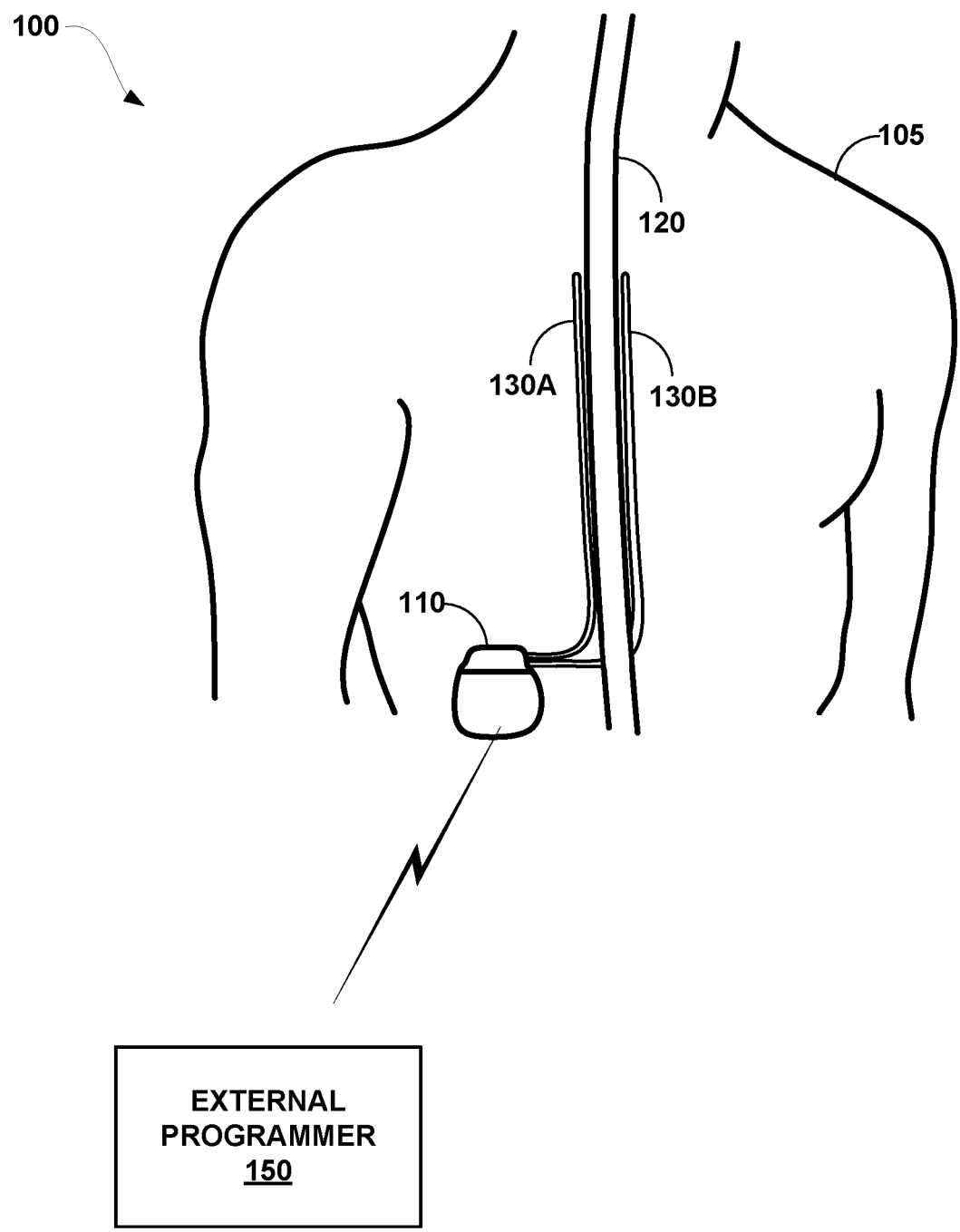
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for auto triggering a lead integrity test based on sensed electrical signals. A system may identify and employ ECAP data to determine the effectiveness of electrical stimulation therapy. For example, the system may use the ECAP data as feedback in a closed-loop control algorithm that controls values of one or more stimulation parameters that at least partially define subsequently delivered stimulation. For example, the system may increase stimulation amplitude in response to determining that an amplitude of an ECAP signal drops below a target ECAP amplitude. However, external noise or internal noise affecting the sensing of ECAP signals may reduce the effectiveness of the closed-loop control algorithm. For example, external noise (e.g., electromagnetic interference (EMI) producing appliances such as microwave ovens, ignition systems, cellular network of mobile phones, lightning, solar flares, and auroras) picked up by recording electrodes may prevent identification of ECAP signals. As another example, internal noise, such as lead integrity issues (e.g., a fractured conductor in the lead, short circuit, integrated circuit problem, or other open circuit), may prevent the detection of ECAP signals. These external or internal noise issues may prevent appropriate ECAP signal measurements and cause the closed-loop control algorithm to not function properly for the patient.

As described herein, devices, systems, and techniques can identify potential problems with ECAP signal detection and mitigate those problems or their effects on the closed-loop control algorithm based on ECAP signals. In one example, a system may compare sensed electrical signals typically used to sense ECAP signals to an expected range of values. For example, the system may expect that one or more characteristic values of the ECAP signal should be within an expected range such as between certain values, below a certain value, or above a certain value. In some examples, the system may determine whether the one or more characteristics of the ECAP signals does not change over a period of time when typical ECAP signals would change. In some examples, the system may compare characteristics of sensed ECAP signals to stored baseline ECAP data. The system may also normalize the ECAP characteristic values based on sensed accelerometer data so that ECAP characteristic values are appropriate for different postures the user may be in (e.g., lying, sitting, or standing).

In response to determining that one or more characteristics of the ECAP signals are outside of the expected range, the system may perform one or more actions to mitigate stimulation therapy issues that may result when using the ECAP signals as a basis for the closed-loop control algorithm. For example, the system may initiate a lead integrity test (on all or a subset of electrodes of the lead) to determine if there are any open circuits that may be causing noise or a lack of signal amplitude that prevents ECAP signal detection. The system may also suspend closed-loop adjustment of stimulation therapy in response to detecting that the ECAP signals are outside of the expected range. This suspension may prevent the system from increasing stimulation amplitude or other parameter caused by the lack of ECAP signals due to an open circuit in sensing, for example. If the lead, or subset of circuits of the lead, pass the lead integrity test, the system may simply temporarily suspend closed-loop stimulation adjustment until the noise in the ECAP signals is no longer detected. If the lead, or subset of circuits of the lead, fail the lead integrity test, the system may suspend or otherwise stop closed-loop stimulation until the system, or a user, reconfigures one or more parameters that defines the closed-loop control algorithm (e.g., using different sensing electrodes or other sensing parameters). In this manner, the system may prevent noise or other issues from causing unintended changes to stimulation therapy and take action to correct those issues for subsequent therapy.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. This electrical stimulation may be delivered in the form of stimulation pulses. In some examples, IMD 110 may be configured to generate and deliver stimulation pulses to include control pulses configured to elicit ECAP signals. The control pulses may or may not contribute to therapy in some examples. In some examples, IMD 110 may, in addition to control pulses, deliver informed pulses that contribute to the therapy for the patient, but which do not elicit detectable ECAPs. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a leads 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, leads 130 may include a lead extension or other segments that may aid in implantation or positioning of leads 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 may be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program). However, in some examples, system 100 changes one or more parameter values automatically based on one or more factors or based on user input.

A closed-loop stimulation program (e.g., a closed-loop control algorithm) may define, based on one or more feedback variables (e.g., one or more characteristics of an ECAP signal), stimulation parameter values that define stimulation pulses (e.g., control pulses and/or informed pulses) delivered by IMD 110 through at least some of the electrodes of leads 130. These stimulation parameter values may include information identifying which electrodes have been selected for delivery of stimulation pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of the closed-loop stimulation program are configured to evoke a compound action potential (e.g., an ECAP signal) from nerves, in the example of control pulses, or contribute to therapy of the patient, in the example of informed pulses. In some examples, the closed-loop stimulation program defines the amplitude of the control and/or informed pulses in response to one or more characteristics of the ECAP signal. For example, an increased amplitude of the ECAP signal may cause the closed-loop stimulation program to reduce the amplitude of the informed pulses and/or control pulses. In other examples, the closed-loop stimulation program may define other parameter values, such as pulse frequency, pulse width, inter-pulse intervals, etc., based on the one or more characteristics of the ECAP signal. In some examples, the adjustments to a parameter of the informed pulses may be tied to (e.g., as a ratio) the same parameter of the control pulses. In some examples, a closed-loop stimulation program may adjust parameter values that define pulses that may, or may not, contribute to therapy for the patient. A single closed-loop stimulation program may control one or more parameter values that define control pulses and informed pulses. In other examples, one closed-loop stimulation program may control parameter values of control pulses while a different closed-loop stimulation program may control parameter values of informed pulses.

Although FIG. 1 is directed to SCS therapy, e.g., used to treat pain, in other examples, system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, leads 130 includes one or more sensors configured to allow IMD 110 to monitor one or more parameters of patient 105, such as patient activity, pressure, temperature, or other characteristics. The one or more sensors may be provided in addition to, or in place of, therapy delivery by leads 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In some examples where ECAP signals cannot be detected from the types of pulses intended to be delivered to provide therapy to the patient, control pulses and informed pulses may be delivered. For example, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. In other examples, a control stimulation pulse may include a tri-phasic pulse or pulse having more than three phases. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. In some cases, the control pulses may elicit an ECAP signal from the tissue, and IMD 110 may sense the ECAP signal via two or more electrodes on leads 130. In some examples, control pulses might not elicit ECAPs that are detectible by IMD 110, however IMD 110 may detect stimulation signals responsive to the control pulses. The control pulses (e.g., detected stimulation signals) may include information that is useful for determining parameters of one or more stimulation delivered to patient 105. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more closed-loop stimulation programs. The one or more closed-loop stimulation programs may be stored in a storage device of IMD 110. Each closed-loop program of the one or more closed-loop stimulation programs includes values for one or more parameters that define an aspect of the control stimulation delivered by IMD 110 according to that program, such as current or voltage amplitude, pulse width, pulse frequency, electrode combination, and, in some examples, timing based on informed pulses to be delivered to patient 105. In some examples, IMD 110 delivers control stimulation to patient 105 according to multiple closed-loop stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, closed-loop stimulation programs, stimulation parameter adjustments, therapy stimulation program selections, closed-loop program selections, user input, or other information to control the operation of IMD 110, e.g., by wireless telemetry or wired connection. As described herein, stimulation delivered to patient 105 may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient (e.g., for home use). A patient programmer may be generally accessible to patient 105 and, in many cases, may be a portable device that may accompany patient 105 throughout the patient's daily routine. For example, a patient programmer may receive input from patient 105 when patient 105 wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Efficacy of electrical stimulation therapy may, in some cases, be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Additionally, or alternatively, efficacy of electrical stimulation therapy may be indicated by one or more characteristics (e.g., a voltage magnitude) of a stimulation signal that is sensed (e.g., the sensed stimulation pulse delivered by IMD 110). The stimulation signal may be representative of the delivered stimulation pulse and related signals instead of action potentials evoked by the delivered stimulation pulse.

In one or more cases where stimulation pulses elicit detectible ECAPs, electrical stimulation therapy delivery by leads 130 of IMD 110 may cause neurons within the target tissue to evoke a compound action potential that travels up and down the target tissue (e.g., nerve fibers), eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

Additionally, or alternatively, the target ECAP value (e.g., the expected range) of characteristic values of the ECAP signal may depend on a posture of patient 105. For example, IMD 110 may include an accelerometer (not illustrated in FIG. 1) which is configured to generate an accelerometer signal. IMD 110 may be configured to determine, based on the accelerometer signal, a posture of patient 105. The determined posture may be a posture of a set of postures including a standing posture, a seated posture, a supine posture, a prone posture, and a side-lying posture, as examples. IMD 110 may be configured to select the expected range of characteristic values of a ECAP signal based on the determined posture of patient 105. As discussed above, in some examples, the IMD 110 may be configured to select the target ECAP value of the ECAP signal based on a magnitude of the stimulation pulse which causes IMD 110 to sense the ECAP signal in addition to selecting the expected range of characteristic values based on the posture of patient 105. In fact, the expected range of characteristic values for a particular ECAP signal may be defined by one or more "transfer functions," where each posture of the set of postures being associated with a respective transfer function.

As described herein, a transfer function may define a relationship between a magnitude of a stimulation pulse which causes IMD 110 to sense an ECAP signal and a target ECAP value of the ECAP signal. Each posture of patient 105 may be associated with a transfer function which defines the respective relationship between stimulation magnitude and the target ECAP value of the ECAP signal. In some examples, one or more transfer functions that are each associated with a respective posture may represent a linear function, meaning that such transfer functions define a linear relationship between the magnitude of a stimulation pulse and the expected range of characteristic values of the ECAP signal resulting from the stimulation pulse. However, this does not need to be the case. Transfer functions may represent any one or combination of functions including linear functions, quadratic functions, exponential functions, piecewise functions, power functions, polynomial functions, rational functions, logarithmic functions, and sinusoidal functions.

In some examples, a standing posture is associated with a first transfer function including a first slope, a sitting posture is associated with a second transfer function including a second slope, and a supine posture is associated with a third transfer function including a third slope. In some examples, the first transfer function, the second transfer function may each represent functions where an expected range of characteristic values of one or more ECAP signal are plotted against a magnitude of a stimulation pulse which causes IMD 110 to sense the respective ECAP signal, where the expected range of characteristic values are plotted on a y-axis of a graph, and the stimulation magnitude is plotted on an x-axis of the graph. In at least some such examples, the first slope of the first transfer function is greater than the second slope of the second transfer function, and the second slope of the second transfer function is greater than the third slope of the third transfer function. Consequently, at times when patient 105 is occupying a supine posture, the target ECAP value (e.g., an expected range of characteristic values) is more sensitive to changes in stimulation amplitude as compared with times when patient 105 is standing or sitting.

Since the first transfer function, the second transfer function, and the third transfer function each have different slopes, IMD 110 may change the target ECAP value (e.g., the expected range of characteristic values) based on detecting a change in the posture of patient 105. For example, in response to IMD 110 determining that patient 105 is standing, IMD 110 may select a first expected range including a first lower-bound value and a first upper-bound value. If stimulation magnitude is held constant and in response to IMD 110 determining that patient 105 is sitting, IMD 110 may select a second expected range including a second lower-bound value and a second upper-bound value. Additionally, if stimulation magnitude is held constant and in response to IMD 110 determining that patient 105 is occupying a supine posture, IMD 110 may select a third expected range including a third lower-bound value and a third upper-bound value. In some examples, the third upper-bound value may be greater than the second upper-bound value and the second upper-bound value may be greater than the first upper-bound value. Additionally, the third lower-bound value may be greater than the second lower-bound value and the second lower-bound value may be greater than the first lower-bound value.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of a ECAP signal to external programmer 150. External programmer 150 may compare a characteristic value of the ECAP signal to the respective expected range of characteristic values, and in response to the comparison, external programmer 150 may instruct IMD 110 to adjust one or more parameters that define the electrical stimulation pulses delivered to patient 105.

In the example techniques described in this disclosure, the control stimulation parameters and the target ECAP value (e.g., an expected range of characteristic values) of the ECAP signals may be initially set at the clinic but may be set and/or adjusted at home by patient 105. Once a target ECAP value (e.g., an expected range of characteristic values) are set, the example techniques allow for automatic adjustment of parameters of the stimulation pulses in order to maintain consistent volume of neural activation and consistent perception of therapy for patient 105 when the electrode-to-neuron distance changes. The ability to change the stimulation parameter values may also allow the therapy to have long term efficacy, with the ability to keep the intensity of the stimulation (e.g., as indicated by the detected ECAP signal) consistent by comparing the measured characteristic values of the ECAP signal to the expected range of characteristic values. IMD 110 may perform these changes without intervention by a physician or patient 105.

In the example techniques described in this disclosure, IMD 110 may comprise stimulation generation circuitry (not shown in FIG. 1) configured to deliver stimulation therapy to a patient. Sensing circuitry (not shown in FIG. 1) may be configured to sense information indicative of one or more evoked compound action potential (ECAP) signals. The processing circuitry may be configured to receive the information indicative of one or more ECAP signals and determine that at least one characteristic value of the one or more ECAP signals is outside of an expected range. The processing circuitry may initiate a lead integrity test for at least one electrode of the medical lead(s) 130 responsive to determining that the at least one characteristic value of the one or more ECAP signals is outside of the expected range. In some examples, the processing circuitry may also suspend closed-loop control of stimulation parameters in response to a characteristic value of the ECAP signals being outside of the expected range. In response to the medical lead passing the lead integrity test, the processing circuitry may temporarily suspend closed-loop control of stimulation parameters and restart closed-loop control after a certain period of time or in response to the characteristic returning to the expected range, for example. In response to the medical lead (or one or more electrodes of the lead) failing the lead integrity test, the processing circuitry may automatically select new electrode combinations for sensing (and delivery of stimulation in some examples) or request a user to select a different electrode combination for sensing (and delivery of stimulation in some examples).

Figure 2:
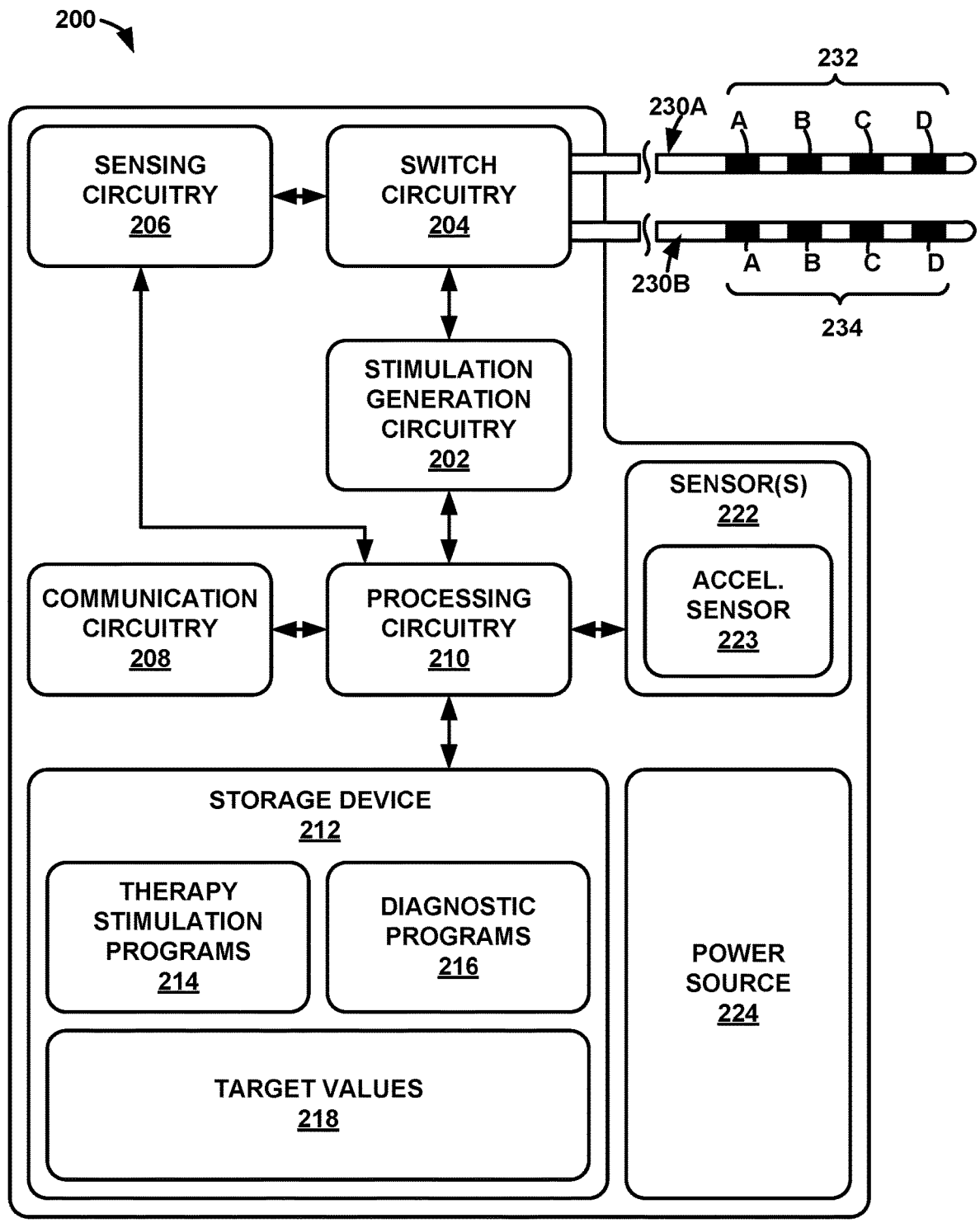
FIG. 2 is a block diagram illustrating an example configuration of components of the IMD of FIG. 1, in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224. As seen in FIG. 2, sensor(s) 222 include acceleration sensor 223.

In the example shown in FIG. 2, storage device 212 stores closed-loop therapy stimulation programs 214 and diagnostic programs 216 in separate memories within storage device 212 or separate areas within storage device 212. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored diagnostic program 216 defines operations for performing lead integrity and closed-loop diagnostics. Diagnostic program 216 may also have additional information such as instructions regarding when to suspend closed-loop therapy, inform the patient 105 to seek assistance or adjust therapy parameters, ask patient 105 questions regarding therapy delivery and perform lead integrity tests.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. Additionally, or alternatively, sensing circuitry 206 may sense one or more stimulation pulses delivered to patient 105 via electrodes 232, 234. In some examples, sensing circuitry 206 detects electrical signals, such ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the closed-loop therapy stimulation programs 214 and diagnostic programs 216 may be stored within storage device 212. Communication circuitry 208 in IMD 200, as well as communication circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to closed-loop therapy stimulation programs 214 and diagnostic programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

In some examples, one or more of electrodes 232 and 234 are suitable for sensing one or more ECAPs. For instance, electrodes 232 and 234 may sense the voltage amplitude of a portion of the ECAP signals, where the sensed voltage amplitude is a characteristic of the ECAP signal.

Storage device 212 may be configured to store information within IMD 200 during operation. Storage device 212 may include a computer-readable storage medium or computer-readable storage device. In some examples, storage device 212 includes one or more of a short-term storage device or a long-term memory. Storage device 212 may include, for example, random access memories (RAM), dynamic random-access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store closed-loop therapy stimulation programs 214, diagnostic programs 216, and target values 218 including baseline ECAP values recorded by a clinician and/or physician.

In some examples, stimulation generation circuitry 202 may be configured to deliver electrical stimulation therapy to patient 105. Stimulation generation circuitry 202 may deliver pulses that evoke detectable responsive ECAPs in the target tissue, the responsive ECAPs propagating through the target tissue before arriving back at electrodes 232, 234. In some examples, a different combination of electrodes 232, 234 may sense responsive ECAPs than a combination of electrodes 232, 234 that delivers stimulation (e.g., recording electrode combinations for sensing ECAPs and stimulation electrode combinations for providing closed loop stimulation therapy). Sensing circuitry 206 may be configured to detect the responsive ECAPs via electrodes 232, 234 and leads 230.

Processing circuitry 210 may periodically or continuously compare sensed one or more characteristic ECAP values to values of an expected range and determine whether the characteristic ECAP values are within an expected range. For example, if processing circuitry 210 detects low or no ECAP amplitude values, then processing circuitry 210 may begin a lead integrity test to determine if lead integrity has been compromised or processing circuitry 210 may compare the ECAP values to a characteristic baseline to determine if noise is masking the ECAP signal.

Processing circuitry 210 analysis of characteristic values from sensed electrical signals is not necessarily directed to determining whether ECAPs are present or not or if some determined data is acceptable or not, although processing circuitry 210 could determine such information in some examples. Instead, processing circuitry 210 may generally search for characteristics of a sensed signal that are outside of expectations, such as target values 218, and perform an action of the characteristic is outside of expectation. For example, if the characteristic values are outside of an expected range, processing circuitry 210 may suspend closed loop stimulation therapy, perform a lead integrity test, or reconfigure stimulation or recording electrode combinations. Processing circuitry 210 monitors values derived from characteristic values of ECAP signals (e.g., values calculated from signals measured as ECAPs), and if they are outside of an expected range, then processing circuitry 210 begins a process to determine if there is a problem (e.g., a lead integrity issue or EMI noise). If a problem is detected, processing circuitry 210 may initiate steps to remedy the problem, such as suspending closed loop stimulation therapy, performing a lead integrity test or reconfiguring stimulation or recording electrodes if they are found to have an integrity issue.

Determining a potential issue, such as lead integrity issues or possible noise, may, in some cases, depend on a posture of patient 105. For example, processing circuitry 210 may be configured to determine a posture of patient 105 based on an acceleration signal generated by acceleration sensor 223. In some examples, acceleration sensor 223 is configured to generate an accelerometer signal. Processing circuitry 210 is configured to identify, based on the accelerometer signal, a posture of a set of postures which patient 105 is occupying.

The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 212. Subsequently, processing circuitry 210 may select, based on the identified posture, an ECAP baseline value (e.g., an expected range of characteristic values) to compare to one or more characteristic ECAP signals sensed by IMD 200 in response to the one or more characteristic ECAP signals being outside of an expected range. For example, if processing circuitry 210 detects one or more characteristic ECAP signals are outside of an expected range, processing circuitry 210 may select an ECAP baseline value obtained at an acceleration signal activity comparable to the sensed acceleration signal of the one or more characteristic ECAP signals which are out outside of the expected range.

In some examples, processing circuitry 210 is configured to identify, based on the accelerometer signal, a posture of a set of postures which patient 105 is occupying while ECAP data is being sensed. Subsequently, processing circuitry 210 may select an expected range of characteristic ECAP baseline values for one or more characteristic values of ECAP signals sensed by sensing circuitry 206 based on the posture of patient 105. For example, target values 218 may include a respective transfer function corresponding to each posture of the set of postures, including a baseline ECAP value at a specific posture.

Target values 218 may include baseline ECAP data (or time domain data clip data) which may be used by diagnostic programs 216 in determining potential lead integrity issues as well as noise being received by electrodes 232 and/or 234. The baseline ECAP data may be or include ECAP data when the patient is at rest, in different postures, or undergoing known aggressors (e.g., ECAP data sensed when the patient is under an aggressor such as different postures or activities such as sneezing or laughing. An aggressor may be a body motion or position that causes a sudden change in ECAP amplitudes (e.g., changing posture, coughing, laughing, or sneezing). In some examples, an ECAP baseline may be performed when a subject is at rest (e.g., sleeping or lying down). When patient 105 is still, then the best recording of a baseline ECAP is possible as any noise from bodily movement is eliminated or substantially reduced. However, in the example above, it may be helpful to know an ECAP baseline when patient 105 is under aggressor. Then processing circuitry 210 may have an aggressor baseline to compare sensed ECAP data to in order to determine whether noise is present or if a normal ECAP signal is present under aggressor. For example, if processing circuitry 210 determines there may be noise masking the ECAP signal or if no ECAP signal is present at all, then the ECAP signal detected may be compared against a baseline ECAP measured in a similar aggressor condition to the patient's current situation. If the ECAP signal and the ECAP baseline are similar, then processing circuitry 210 may determine there is an ECAP signal present and it is under aggressor. If the ECAP signal and ECAP baseline are dissimilar, then processing circuitry may determine there is another issue (e.g., such as a broken or cracked lead or electrode). In any case, the baseline ECAP data may include acceptable ECAP data as opposed to ECAP data that may be indicative of noise or other sensing issue. Accelerometer data (for aggressors in which accelerometers may detect the body motion) may be correlated with ECAP data under aggressors and stored as baselines for correlation purposes. Thus, if processing circuitry 210 detects an increase in ECAP amplitude, this elevated ECAP amplitude may be compared with a baseline stored with similar accelerometer data and determine if the elevated ECAP amplitude correlates to the activity of patient 105 or if the elevated ECAP amplitude is due to noise or a potential lead integrity issue.

The baseline ECAP data may also correlate with accelerometer data which is recorded concomitantly with the sensed ECAP signals from which the baseline ECAP data is derived. The ECAP or accelerometer data may be recorded and set as baseline ECAP data in a clinic setting when IMD 200 is first programmed for patient 105. However, baseline ECAP data or accelerometer data may also be collected during the lifetime of IMD 200 (e.g., patient 105 may monitor and save these values through a programmer similar to external programmer 150). The accelerometer data is not necessary to establish an ECAP data baseline; however, as discussed above, IMD 200 may analyze accelerometer data to confirm patient movement with ECAP data having characteristic values out of a range compared to ECAP data baseline data taken when patient 105 is sedentary or in a prone position. That is, IMD 200 may select an ECAP data baselines stored for a respective patient activity (e.g., from multiple different ECAP data baselines stored for different respective patient activities) to determine whether a lead integrity issue exists or if patient 105 is in an aggressor state.

As discussed in detail below, baseline ECAP data can be used in an effort to determine whether ECAP data is representative of actual patient conditions or if the ECAP data is representative of noise instead of patient conditions during normal operation of closed-loop therapy stimulation program 214. For example, in situations where patient 105 is in a noisy EMI environment, EMI noise may be masking (e.g., covering up) actual physiological signals representative of nerve activity making it difficult for processing circuitry 210 to identify actual nerve activity from the ECAP data recorded by electrodes 232, 234 to sense the ECAP data. By using one or more characteristic signals of ECAP baseline data and comparing it to one or more characteristic signals sensed by electrodes 232, 234, processing circuitry 210 may determine whether the ECAP signal is representative of nerve activity or noise that masks the nerve activity. In the event one or more characteristic values of ECAP data is outside of an expected range or if one or more characteristic values of ECAP data have had a variance for a period of time, diagnostic program 216 may use a stored baseline value from target values 218 to determine if an issue exists (e.g., a lead integrity issue or noise masking issue). Further, with correlated accelerometer data, diagnostic program 218 may use baseline ECAP data which correlates with the current posture and/or activity level of patient 105 at the time diagnostic program 216 is executing.

In some examples, processing circuitry 210 is configured to determine, based on the accelerometer signal generated by acceleration sensor 223, whether accelerometer data indicates a regular circadian rhythm. Processing circuitry 210 may be configured to determine whether electrodes 232, 234 are functioning properly based on stored ECAP data and accelerometer data. For example, if ECAP data has been below a threshold throughout the day but, the accelerometer data indicates a regular circadian rhythm (e.g., patient 105 is performing normal daily functions and not sleeping), processing circuitry 210 may initiate a lead integrity test to determine if electrodes 232, 234 or other components of the lead or device (e.g., conductors that electrically connect the electrodes to IMD 200) are functioning properly.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

In some examples, medical device 200 with stimulation generation circuitry 202 configured to deliver a closed-loop stimulation to patient 105 and sensing circuitry 206 configured to sense information indicative of one or more ECAP signals, may be configured to, with processing circuitry 210, receive the information indicative of one or more ECAP signals. Processing circuitry 210 may verify the one or more ECAP signals against a baseline ECAP, stored in target values 218, and determine that at least one characteristic value of the one or more ECAP signals is outside of an expected range. Processing circuitry 210 may initiate a lead integrity test for the medical lead responsive to determining that the at least one characteristic value of the one or more ECAP signals is outside of the expected range. Processing circuitry 210 may diagnose lead integrity issues or noise picked up by the sensing electrodes based upon the lead integrity test, the received one or more ECAP signals, and the baseline ECAP data.

Figure 3:
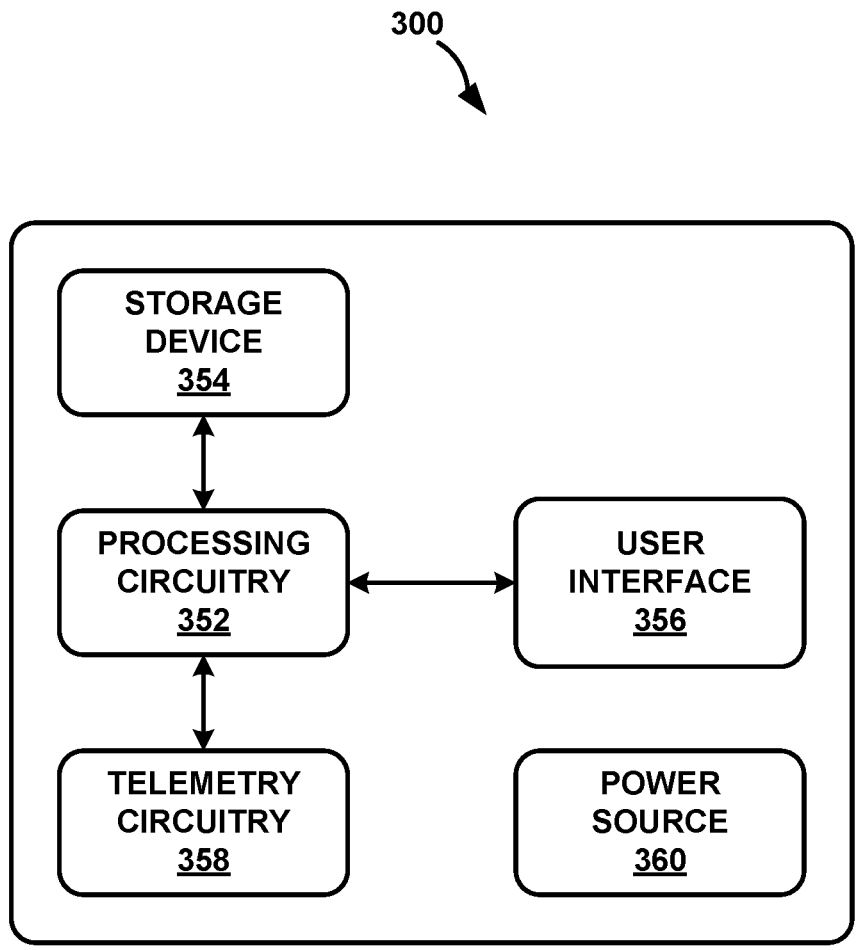
FIG. 3 is a block diagram illustrating an example configuration of components of the external programmer of FIG. 1, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses and baseline ECAP values. Storage device 354 may also store data received from a medical device (e.g., IMD 110). For example, storage device 354 may store stimulation signal and/or ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 may present a graphic display requesting updates to the closed loop therapy program or therapy stimulation programs 214. External programmer 300 may generate this update in response to receiving an alert from IMD 200 (e.g., an alert regarding a failed lead integrity test). External programmer 300 may receive an indication from a clinician instructing a processor of the medical device to update one or more closed-loop therapy stimulation programs 214 or to update one or more diagnostic programs 216. Updating closed-loop therapy stimulation programs 214 and diagnostic programs 216 may include changing one or more parameters of the stimulation pulses delivered by the medical device according to the programs, such as reconfiguration of an electrode combination (e.g., modifying a current electrode combination or selecting a different electrode combination) to not include an electrode associated with a filed lead integrity test, and other variables such as amplitude, pulse width, frequency, and pulse shape of the informed pulses and/or control pulses. User interface 356 may also receive instructions from the clinician commanding any electrical stimulation, including control pulses and/or informed pulses to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

Figure 4:
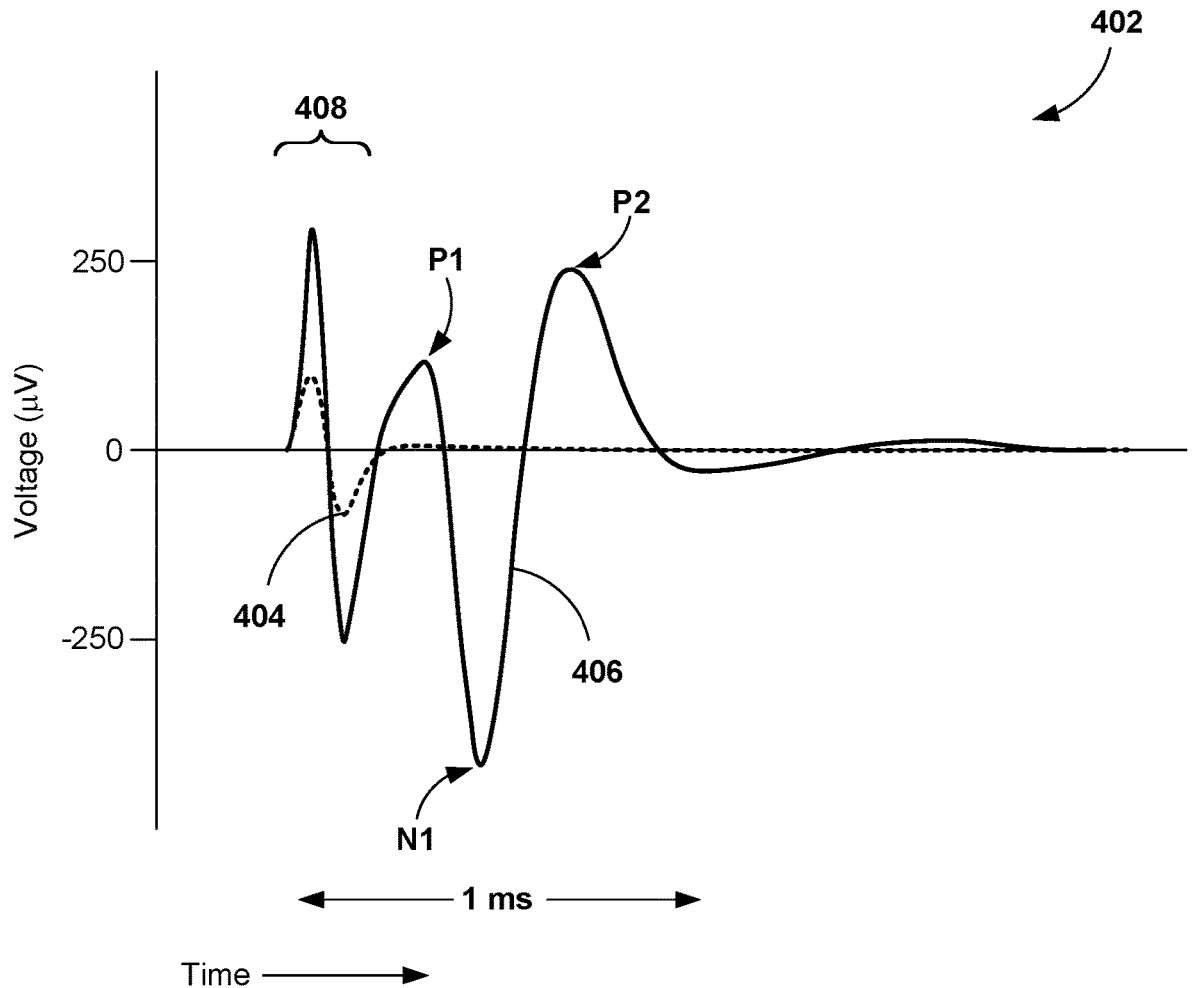
FIG. 4 is a graph 402 of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from stimulation pulses that were delivered from a guarded cathode, where the stimulation pulses are biphasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. It is noted that monophasic, tri-phasic, or pulses with another quantity of phases may be in other examples.

Peaks 408 of ECAP signal 404 are detected and represent artifacts of stimulation signals of the delivered stimulation pulse. However, no propagating signal is detected after the stimulation signal in ECAP signal 404 because the stimulation pulse had an intensity (e.g., an amplitude and/or pulse width) that was "sub-threshold" or below a detection threshold (e.g., a sub-detection threshold) and/or below a propagation threshold (e.g., a sub-propagation threshold).

In contrast to ECAP signal 404, ECAP signal 406 represents the voltage amplitude detected from a supra-detection stimulation threshold stimulation pulse. Peaks 408 of ECAP signal 406 are detected and represent stimulation signals of the delivered stimulation pulse. After peaks 408, ECAP signal 406 also includes peaks P1, N1, and P2, which are three typical peaks representative of propagating action potentials from an ECAP. The example duration of the stimulation signal and peaks P1, N1, and P2 is approximately 1 millisecond (ms).

When detecting the ECAP of ECAP signal 406, different characteristics may be identified. For example, the characteristic of the ECAP may be the amplitude between N1 and P2. This N1-P2 amplitude may be easily detectable even if the stimulation signal impinges on P1, a relatively large signal, and the N1-P2 amplitude may be minimally affected by electronic drift in the signal. In other examples, the characteristic of the ECAP used to control subsequent stimulation pulses may be an amplitude of P1, N1, or P2 with respect to neutral or zero voltage. In some examples, the characteristic of the ECAP used to control subsequent stimulation pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2.

The time between when the stimulation pulse is delivered and a point in the ECAP signal may be referred to as a latency of the ECAP and may indicate the types of fibers being captured by the stimulation pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the stimulation pulse, as long as the pulse amplitude is greater than threshold such that nerves depolarize and propagate the signal. The target ECAP characteristic (e.g., the target ECAP amplitude) may be determined from the ECAP signal detected from a stimulation pulse (or a control pulse) when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5:
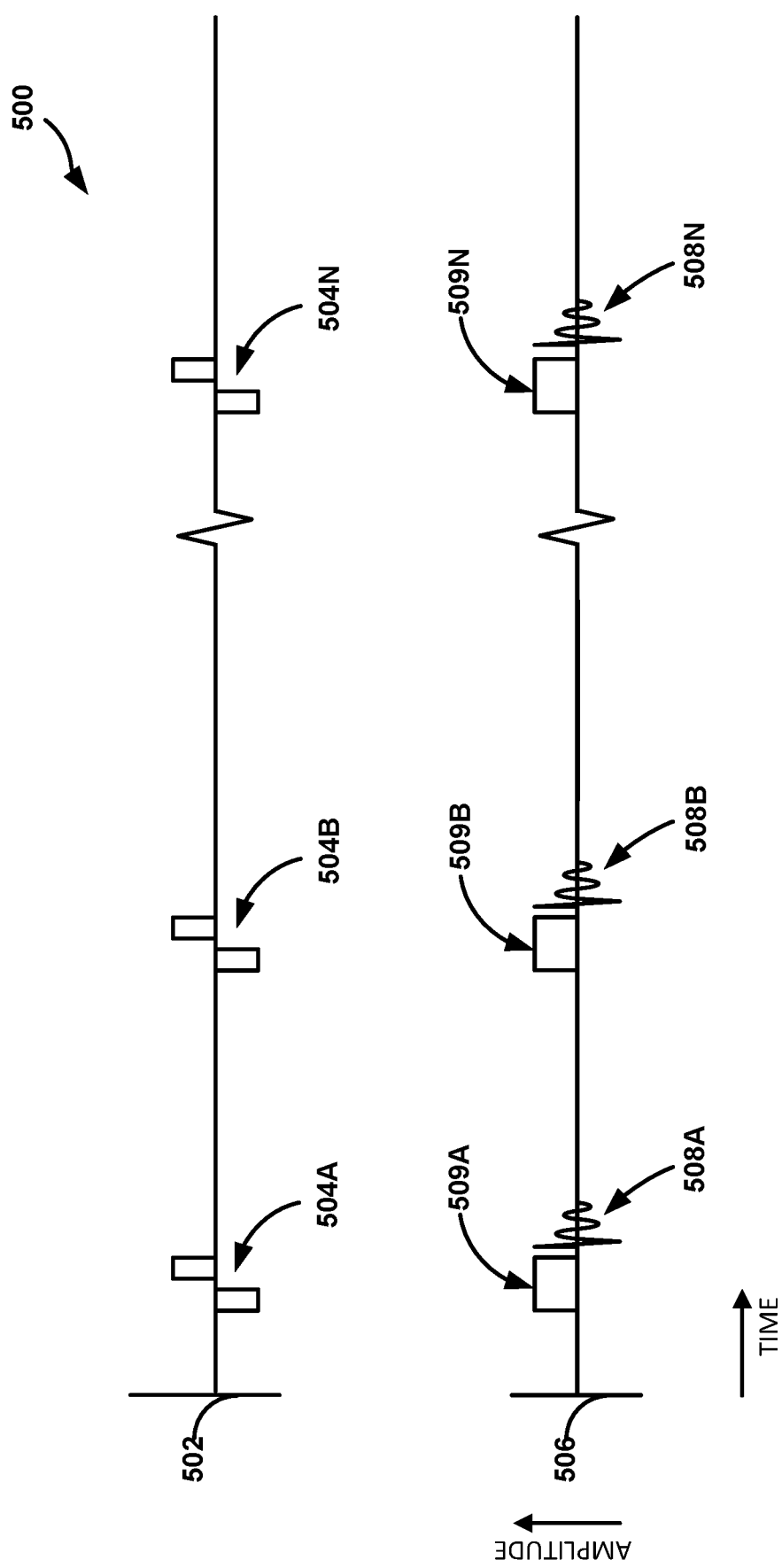
FIG. 5 is an example timing diagram illustrating an example of electrical stimulation pulses, respective stimulation signals, and respective sensed ECAPs, in accordance with one or more techniques of this disclosure.

FIG. 5 is a timing diagram 500 illustrating an example of electrical stimulation pulses, respective stimulation signals, and respective sensed ECAPs, in accordance with one or more techniques of this disclosure. For convenience, FIG. 5 is described with reference to IMD 200 of FIG. 2. As illustrated, timing diagram 500 includes first channel 502, a plurality of stimulation pulses 504A-504N (collectively "stimulation pulses 504"), second channel 506, a plurality of respective ECAPs 508A-508N (collectively "ECAPs 508"), and a plurality of stimulation signals 509A-509N (collectively "stimulation signals 509"). Stimulation pulses 504 may represent any type of pulse that is deliverable by IMD 200. In the example of FIG. 5, IMD 200 may deliver therapy with control pulses instead of, or without, informed pulses.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Stimulation pulses 504 may be electrical pulses delivered to the spinal cord of the patient by at least one of electrodes 232, 234, and stimulation pulses 504 may be balanced biphasic square pulses with an interphase interval. In other words, each of stimulation pulses 504 are shown with a negative phase and a positive phase separated by an interphase interval. For example, a stimulation pulse 504 may have a negative voltage for the same amount of time and amplitude that it has a positive voltage. It is noted that the negative voltage phase may be before or after the positive voltage phase. Stimulation pulses 504 may be delivered according to closed-loop therapy stimulation programs 214 stored in storage device 212 of IMD 200, and closed-loop therapy stimulation programs 214 may be updated according to user input via an external programmer and/or may be updated according to a signal from sensor(s) 222. In one example, stimulation pulses 504 may have a pulse width of less than approximately 300 microseconds (e.g., the total time of the positive phase, the negative phase, and the interphase interval is less than 300 microseconds). In another example, stimulation pulses 504 may have a pulse width of approximately 100 μs for each phase of the biphasic pulse. As illustrated in FIG. 5, stimulation pulses 504 may be delivered via channel 502. Delivery of stimulation pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to stimulation pulses 504. ECAPs 508 are electrical signals which may propagate along a nerve away from the origination of stimulation pulses 504. In one example, ECAPs 508 are sensed by different electrodes than the electrodes used to deliver stimulation pulses 504. As illustrated in FIG. 5, ECAPs 508 may be recorded on second channel 506.

Figure 6:
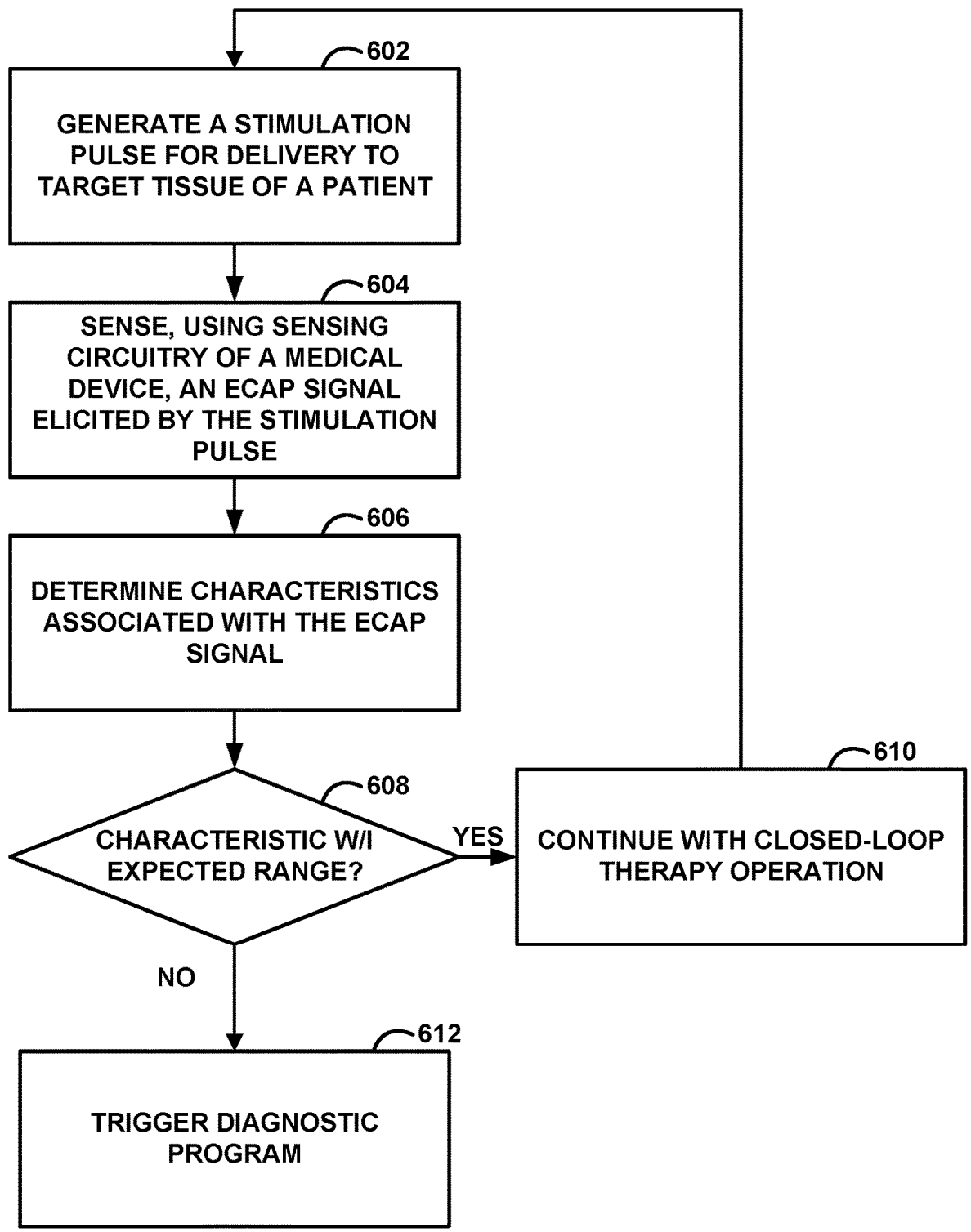
FIG. 6 is a flow diagram illustrating an example operation for controlling stimulation based on one or more ECAP signals, in accordance with one or more techniques of this disclosure.

FIG. 6 is a flow diagram illustrating an example operation for controlling stimulation based on one or more ECAP signals, in accordance with one or more techniques of this disclosure. FIG. 6 is described with respect to IMD 200 of FIG. 2. However, the techniques of FIG. 6 may be performed by different components of IMD 200 or by additional or alternative medical devices.

In the example of FIG. 6, stimulation generation circuitry 202 is configured to generate a stimulation pulse for delivery to target tissue of patient 105 (602). In some examples, stimulation generation circuitry 202 is configured to generate the stimulation pulse according to closed-loop therapy stimulation programs 214. In some examples, closed-loop therapy stimulation programs 214 may include one or more parameter values which define stimulation pulses delivered by IMD 200. Sensing circuitry 206 may sense an ECAP signal elicited by the stimulation pulse delivered to the target tissue of patient 105 (604).

Processing circuitry 210 may determine one or more characteristic values associated with the ECAP signal (606). Amplitude between two peaks of the ECAP signal (e.g., between N1 and P2) is one example of a characteristic of the ECAP signal. A variance in amplitude over an extended period of time is another example of a characteristic of the ECAP signal. A frequency variance over a short period of time is another example of a characteristic of the ECAP signal. Processing circuitry 210 may determine whether the characteristic values associated with the ECAP signal is within an expected range of ECAP signal characteristic values (608). The expected range of ECAP signal characteristic values may also include the absence of variations in the ECAP signal characteristics over short and long time periods. In some examples, processing circuitry 210 may select the expected range of ECAP signal characteristic values from storage device 212 or target values 218. For example, processing circuitry 210 may select the expected range of ECAP signal characteristic values based on a determined posture of patient 105 and an amplitude of the stimulation pulse which causes IMD 200 to sense the ECAP signal. In response to determining that the characteristic values associated with the ECAP signal is within the expected range of ECAP signal characteristic values ("YES" branch of block 608), processing circuitry 210 may continue with normal closed-loop therapy operation (610) and continue to generate stimulation pulses (602). The expected range of ECAP signal characteristic values may be a larger range and involve more or different characteristic values than an amplitude range as compared to target values 218 for the therapy stimulation programs 218. For example, if the ECAP signal characteristic values are outside of target ECAP values, the closed-loop programming may increase or decrease stimulation amplitude. In contrast, the expected range for the ECAP signal characteristic values discussed in FIG. 6 may be a larger range and involve different or additional parameters, such as variance, than the target ECAP values for the closed-loop programming where being outside the expected range signifies that something is wrong, and lead integrity may be an issue. Thus, for purposes of the description expected range of ECAP signal characteristic values is an equal or broader range than the target ECAP values in the closed-loop therapy stimulation programs 214.

In response to determining that the ECAP signal characteristic values associated with the ECAP signal are not within the expected range of ECAP signal characteristic values ("NO" branch of block 608), processing circuitry 210 may determine whether the ECAP signal characteristic has been outside the expected range for a predefined period of time. The predefined period of time may be set and stored in target values 218 and may depend on the ECAP signal characteristic values that are outside of the expected range. The predefined period may be in terms of time. For example, if an ECAP signal characteristic amplitude has been below 10 μV throughout a twenty-four-hour period("No" branch of block 608), this may trigger diagnostic program 216 to determine why the ECAP signal characteristic amplitude is low for so long, such as a lead integrity test (612). In another example, if an ECAP signal characteristic amplitude remains above an upper limit of the expected range of ECAP characteristic values after stimulation amplitude has decreased to a lower or zero threshold ("NO" branch of block 608), this may trigger diagnostic program 216 to determine why the ECAP amplitude has remained high when it should be showing a decrease (612). The predefined period may be in terms of detecting a variance. For example, if an ECAP signal characteristic amplitude has presented a variance sustained over a prolonged period of time without triggering a closed-loop state change ("NO" branch of block 608), this may trigger diagnostic program 216 to determine why the ECAP amplitude is so erratic (612), but yet not at levels to initiate a closed-loop state change). In another example, if an ECAP signal characteristic amplitude has a large amount of variance over a short period of time, possibly indicating a fractured conductor or a fractured electrode, this may trigger diagnostic program 216 to run a lead integrity test to determine if there is a lead fracture issue.

In response to determining that the ECAP signal characteristic values are not outside of the expected range for a predefined period of time ("NO" branch of block 608), then closed-loop therapy stimulation program 214 continues with closed-loop therapy (610) and the system may continue to generate stimulation pulses (602). For example, processing circuitry 210 may adjust stimulation amplitude based on the characteristic of the ECAP signal. In response to determining that the ECAP signal characteristic values are outside of the expected range, outside of the expected range for greater than a predefined period of time or have a long or short term variation in the ECAP signal characteristic values ("NO" branch of block 608), then diagnostic program 216 is executed to troubleshoot why the ECAP signal is outside of the expected range (612). Diagnostic program 216 may include a lead integrity test for one or more current paths of the lead and/or other analyses.

Figure 7:
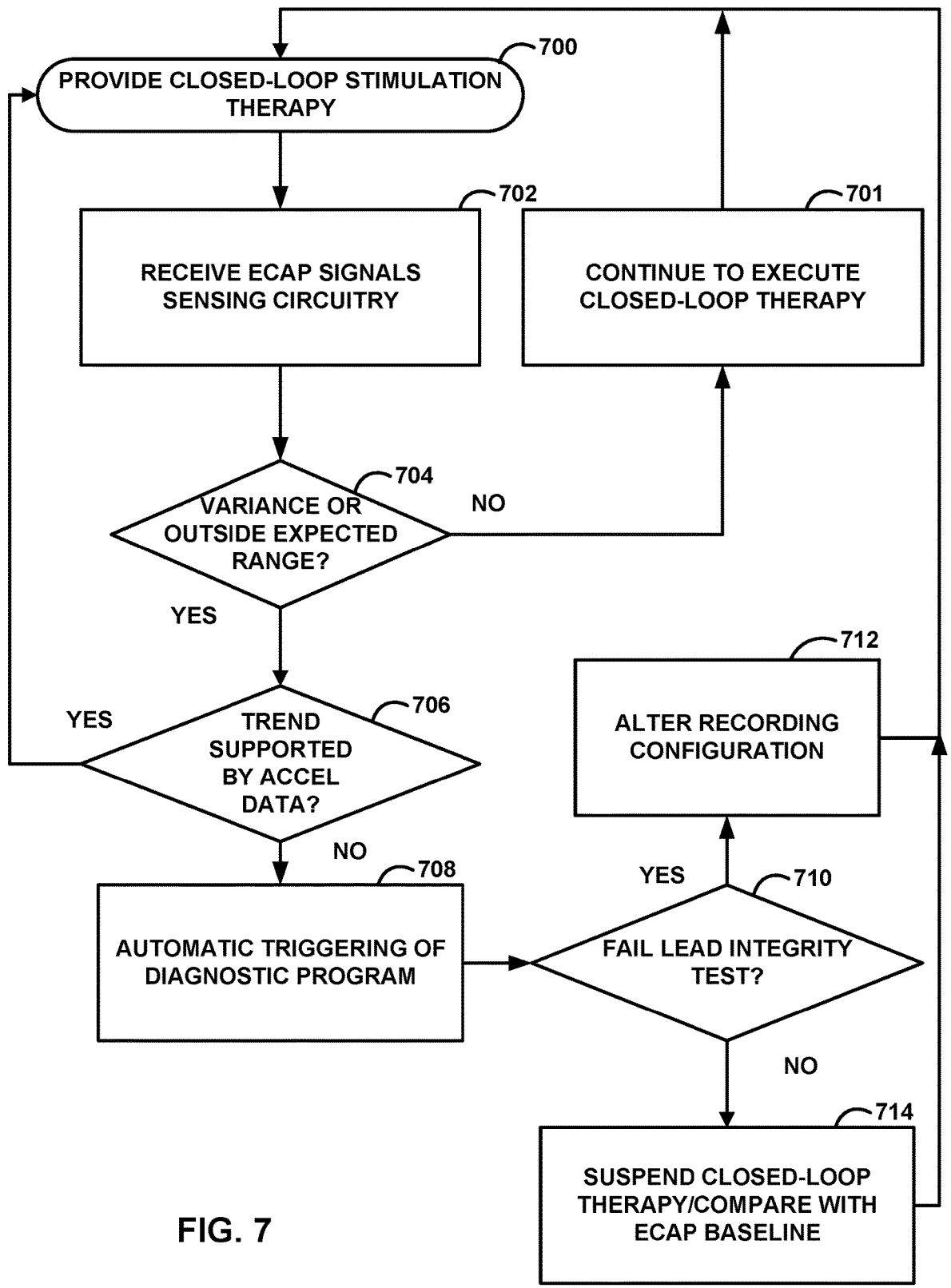
FIG. 7 is a flow diagram illustrating an example operation of an auto-triggered diagnostic based on one or more ECAP signals, in accordance with one or more techniques of this disclosure.

FIG. 7 is a flow diagram illustrating an example operation of an auto-triggered diagnostic based on one or more ECAP signals, in accordance with one or more techniques of this disclosure. As discussed above, when closed-loop therapy stimulation program 214 is used, various factors, such as lead integrity issues or noise (e.g., EMI) picked up by recording electrodes, may contribute to closed-loop therapy stimulation program 214 not functioning properly due to inaccurate information inputted through the feedback path (e.g., the sensed ECAP signals). In examples of the present disclosure, a baseline ECAP, a time domain data clip, or a baseline ECAP with a time domain data clip may be stored within target values 218. Target ECAP signal characteristic values or expected ranges of ECAP characteristic values for each posture may be stored as well along with accelerometer data indicative of each posture. Processing circuitry 210 may execute diagnostic programs 216 to use this information to determine whether there is a lead integrity issue or if noise is corrupting the ECAP signal as described below.

In operation, processing circuitry 210 may perform closed-loop stimulation according to therapy stimulation program 214 (e.g., according to FIG. 6) to provide stimulation therapy to patient 105 (700). Processing circuitry 210 may receive information from sensing circuitry 206 indicative of one or more ECAP signal characteristic values sensed by at least one electrode 232 and/or 234 carried by a medical lead 230 (702). Processing circuitry 210 may determine that at least one ECAP signal characteristic value of the received ECAP signal characteristic values is outside of an expected range, outside of an expected range for greater than a predefined period of time, or the ECAP signal characteristic values have short or long term variances (704). For example, this outside of range may include an unexpected ECAP signal characteristic trend or other unexpected change or value in sensed data. If the ECAP signal characteristic values are within the expected range ("NO" branch of block 704), then closed-loop therapy stimulation program 214 may continue to execute closed-loop therapy (701) and the example operation may return to block 700. If the ECAP signal characteristic values are outside of the expected range ("YES" branch of block 704), processing circuitry 210 may determine if accelerometer data supports the determined ECAP signal characteristic values (706).

For example, the amplitude of one or more ECAP signals may have a low amplitude like ECAP signal 404 (FIG. 4). IMD 200 may save and examine ECAP signal amplitude data in target values 218 for comparison with later gathered ECAP data. If an ECAP amplitude has been outside of the expected range of amplitudes, for example below 10 µV for a predetermined amount of time (e.g., minutes or hours), accelerometer data may be checked to verify a posture of patient 105 or to examine a circadian rhythm of patient 105. In response to determining that the at least one characteristic value of the one or more ECAP signals is outside of the expected range, processing circuitry 210 may determine if accelerometer data indicates a circadian rhythm is within a normal circadian rhythm range (706). That is, is the ECAP characteristic value being outside of the expected range consistent with the accelerometer data. For example, patient 105 sleeping may be consistent with low ECAP characteristic values and not necessitate any further diagnostic testing.

If the accelerometer data supports a circadian rhythm correlating with the ECAP signal characteristic values, then diagnostic program 216 may return to normal operation of the closed-loop therapy program 214 ("YES" branch of block 706). If the accelerometer data does not support a circadian rhythm of the ECAP signal characteristic values (e.g., the accelerometer indicates patient 105 is in a strenuous activity) then diagnostic program 216 is triggered ("NO" branch of block 706) (708).

Processing circuitry 210 may initiate a lead integrity test for medical lead 230 (710). The lead integrity test may include, but is not limited to, an electrode impedance measurement with low amplitude (i.e., amplitude below a perception threshold by patient 105, saved in target values 218 from a prior clinic visit) test pulse of all electrodes 232 and/or 234 or only a subset of electrodes, such as the electrodes involved in sensing electrode combinations and, in some examples, stimulation electrode combinations.

If an electrode integrity issue is found ("Yes" branch of block 710) on at least one recording electrode, therapy program 214 may alter the recording configuration eliminating any electrode with an integrity issue (712). In another example, if the electrode integrity test discovers integrity issues with at least one stimulation electrode, IMD 200 may instruct patient 105, possibly through user interface 356, to seek out clinician assistance for a potential reprogram of IMD 200.

If no lead integrity issue was discovered, then diagnostic program 216 suspends closed-loop therapy program 214 and begins a periodic comparison with an ECAP signal baseline characteristic value until an ECAP signal characteristic value is found ("NO" branch of block 710) (714). Once the ECAP signal characteristic values are found to be within a tolerance of the ECAP signal baseline characteristic value, closed-loop therapy 214 may resume (700).

Figure 8:
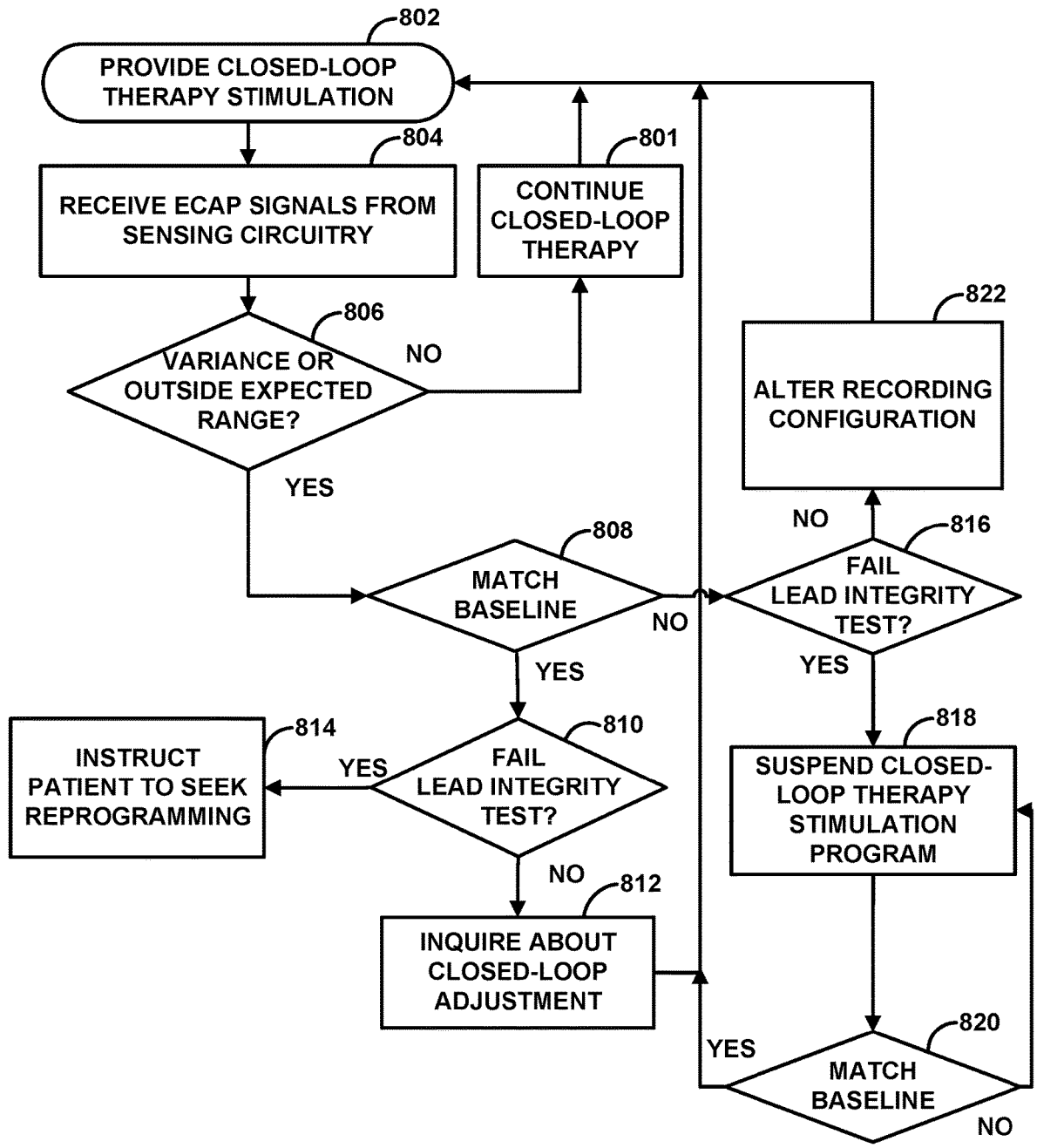
FIG. 8 is a flow diagram illustrating an example operation for an auto-triggered diagnostic based upon ECAP data, in accordance with one or more techniques of this disclosure.

FIG. 8 is a flow diagram illustrating an example operation for triggered diagnostics based upon ECAP data, in accordance with one or more techniques of this disclosure. During normal operation processing circuitry 210 may operate closed-loop therapy stimulation program 214 (802). Processing circuitry 210 may receive one or more ECAP signals from sensing circuitry 206 and electrodes 232 and/or 234 (804). Processing circuitry 210 may determine if the ECAP signals are outside the expected range for greater than the predetermined amount of time (806). The expected range may vary for every patient and the expected range may vary along with changes in the closed-loop program. For example, when the ECAP signal is above a threshold, stimulation amplitude may be decreased. Responding to the decrease in stimulation amplitude, the ECAP may also decrease. If the stimulation amplitude is substantially decreased (e.g., down to 0 volts (V)) and the ECAP signal is still showing a large amplitude, then the signal being sensed may be noise and not an ECAP signal. Outside of the expected range values may be a value above the closed-loop algorithm threshold, such as the example just provided. In another example, the expected range may be any signal from 0 microvolts (µV) to 30 µV. In other examples, the expected range may be any signal from 0 µV to 20 µV. In yet other examples, the expected range may be any signal from 0 µV to 10 µV.

If ECAP signals are outside of the expected range for greater than the predetermined amount of time, processing circuitry 210 may suspend closed-loop therapy and initiate diagnostic program 216 ("YES" branch of block 806). If ECAP signals are all within the expected range, then closed-loop therapy stimulation program 214 may continue closed-loop stimulation therapy 214 (801) ("NO" branch of block 806) and the example operation may return to block 802.

In a situation where one or more of the ECAP signal characteristic values are outside the expected range for a predetermined period of time ("YES" branch of block 806), then the ECAP signal characteristic values may be compared to the ECAP baseline characteristic value (808). For example, when stimulation amplitude has been decreased to a lower threshold or has been lowered to zero, but an ECAP signal characteristic values are still above an upper limit, a template matching check may be triggered. Diagnostics program 216 may identify if an ECAP signal characteristic value is actually present in the sensed ECAP signal characteristic values or if the sensed signal is actually noise (808).

If the sensed one or more ECAP signal characteristic values is outside of an expected characteristic threshold, processing circuitry 210 may compare the one or more sensed ECAP signal characteristic values to a baseline ECAP characteristic value stored in target values 218 (808). Processing circuitry 210 may verify whether the one or more ECAP signals are one of either noise or verified one or more ECAP signal characteristic values as compared against the baseline ECAP characteristic value.

If processing circuitry 210 determines an ECAP signal is present ("YES" branch of block 808), as it matches or significantly matches the baseline ECAP characteristic value, processing circuitry 210 may perform a lead integrity test of the stimulation electrodes 232 and/or 234 to determine the presence of a fractured lead or electrode providing only intermittent ECAP characteristic values (810). During the lead integrity test, processing circuitry 210 may ask patient 105 to indicate if they are perceiving any overstimulation while conducting a low amplitude impedance measurement of the stimulation electrodes. If no issue is found with the stimulation electrodes 232 and/or 234 during the electrode integrity check ("NO" branch of block 810), processing circuitry 210 may ask patient 105 if an adjustment to closed-loop therapy program 214 is needed (812). Patient 105 may then interact with user interface 356 of external device 300 and adjust the closed-loop therapy stimulation program 214 and return to closed-loop therapy stimulation (802).

If an open or fractured circuit is found with the stimulation electrodes during the lead integrity test (e.g., meaning a lead or a stimulation electrode is faulty)("YES" branch of block 810), processing circuitry 210 may transmit a request to programmer 150 to prompt patient 105 to seek out a clinician and ask for potential reprogram of closed-loop therapy program 214 (814).

If the ECAP value cannot be verified as being an actual ECAP signal ("NO" branch of block 808), it may be possible the ECAP signal characteristic values are actually noise being recorded by the recording electrodes. Processing circuitry 210 may then perform a lead integrity test on both the stimulation and recording electrodes (816).

If both the stimulation and recording electrodes pass the lead integrity test ("YES" branch of block 816), processing circuitry 210 may suspend closed-loop therapy stimulation program 214 (818) and re-conduct baseline matching (820) periodically until an ECAP signal characteristic values is found or until a recorded signal matches or significantly matches the baseline signal characteristic value ("NO" branch of block 818). In an example, the initial periodicity for baseline matching may have a resolution of minutes (e.g., from 1 to 2 minutes) and may increase in frequency gradually over time in some examples. In other examples, the periodicity may be up to an hour or more, however, if the suspected noise hasn't dissipated in a short period of time, then the system may determine that there is a different issue causing the problem, such as a fractured lead.

Once one or more ECAP signals are found, closed-loop therapy stimulation program 214 may resume operation ("YES" branch of block 820) (802). Often times, this may be a matter of allowing an EMI noise source to stop operating or for patient 105 to distance themselves from the noise source. For example, once diagnostic program 216 determines there may be noise masking the ECAP signal characteristic values (818) IMD 200 may transmit an alert to programmer 300, and in response to receiving the alert, user interface 356 may, instruct patient 105 to look around for possible sources of EMI noise and to move away from them briefly.

If an open circuit is found with a recording electrode 232 and/or 234 ("NO" branch of block 816), closed-loop therapy stimulation program 214 may be instructed to alter the recording electrode configuration (822). Diagnostic program 216 then returns operation to closed-loop therapy stimulation program 214 (802).

Figure 9:
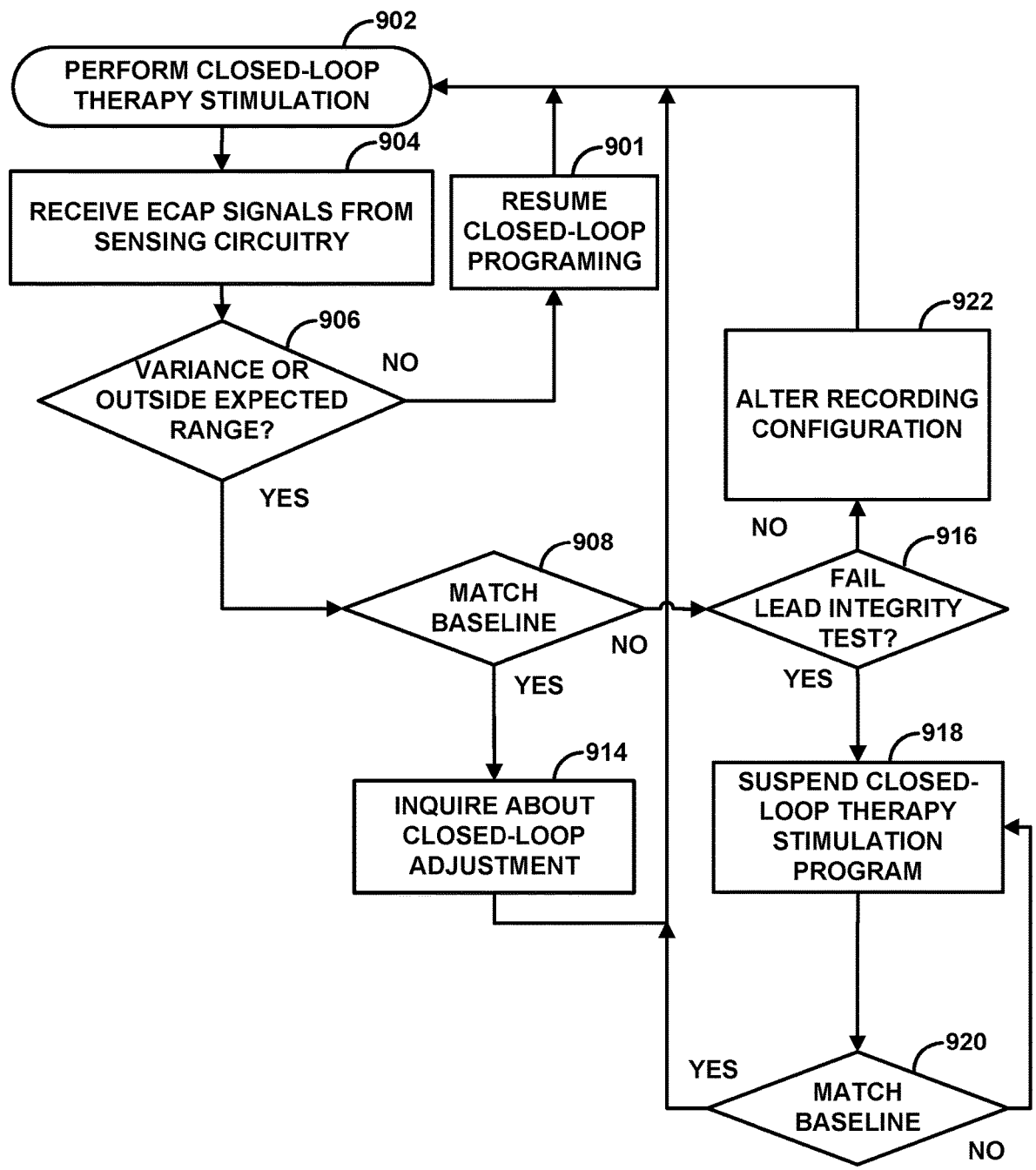
FIG. 9 is a flow diagram illustrating an example operation for an auto-triggered diagnostic based on ECAP data, in accordance with one or more techniques of this disclosure.

FIG. 9 is a flow diagram illustrating an example operation for diagnostics based on ECAP data indicating potential EMI noise, in accordance with one or more techniques of this disclosure. During normal operation processing circuitry 210 may perform closed-loop therapy stimulation program 214 (902). Processing circuitry 210 may receive one or more ECAP signal characteristic values from sensing circuitry 206 and electrodes 232 and/or 234 (904). Processing circuitry 210 may evaluate the one or more ECAP signal characteristic values to determine if the one or more ECAP signal characteristic values is showing a variance outside of the expected range for greater than the predefined period of time (906). If one or more ECAP signal characteristic values are showing a long-term variance or a high frequency short term variance outside of the expected range ("YES" branch of block 906) diagnostic program 216 may be automatically triggered. If ECAP signals are all within the expected range for the predefined amount of time, then closed-loop therapy stimulation may resume operation (901) and the example operation may return to block 902.

In situations where sensed ECAP characteristic values are showing a large amount of variance sustained over a prolonged period of time, without the triggering changes in stimulation parameters, diagnostic program 216 may compare one or more ECAP signal characteristic values with a baseline ECAP signal characteristic value and verify if an ECAP signal may be present (908).

If no ECAP signals are detected ("NO" branch of 908), an electrode integrity test may be performed on the recording and stimulation electrodes 232 and/or 234 (916). If both the recording and stimulation electrodes 232 and/or 234 pass the integrity test ("YES" branch of 916), then closed-loop therapy stimulation programming may be temporarily suspended (918). During stimulation suspension another baseline ECAP matching test may be performed periodically (920) until one or more ECAP signal characteristic values may be matched or one or more collected signals substantially matches the saved baseline signal ("NO" branch of 920). Once one or more ECAP signal characteristic values is matched or substantially matched, then closed-loop therapy stimulation program 214 may be reengaged ("YES" branch of 920) (902).

If an open circuit or damaged electrode is found with the recording electrodes 232 and/or 234, ("NO" branch of 916), then diagnostic program 216 may instruct closed-loop therapy stimulation program 214 to alter the recording configuration (922) and return to normal closed-loop therapy stimulation programing (902). If an open circuit or damaged electrode is found with the stimulation electrodes 232 and/or 234 ("NO" branch of 916), then diagnostic program 216 instructs closed-loop therapy stimulation program 214 to suspend therapy and patient 105 may be instructed through user interface 356 to seek out reprogramming of closed-loop therapy stimulation program.

If the ECAP signal characteristic values are matched ("YES" branch of 908), then diagnostic program 216 may suspend closed loop operation and instruct patient 105 to determine if an adjustment to closed-loop therapy stimulation program 214 may be needed (914). If so, then patient 105 may follow an at home reprogramming process.

Figure 10:
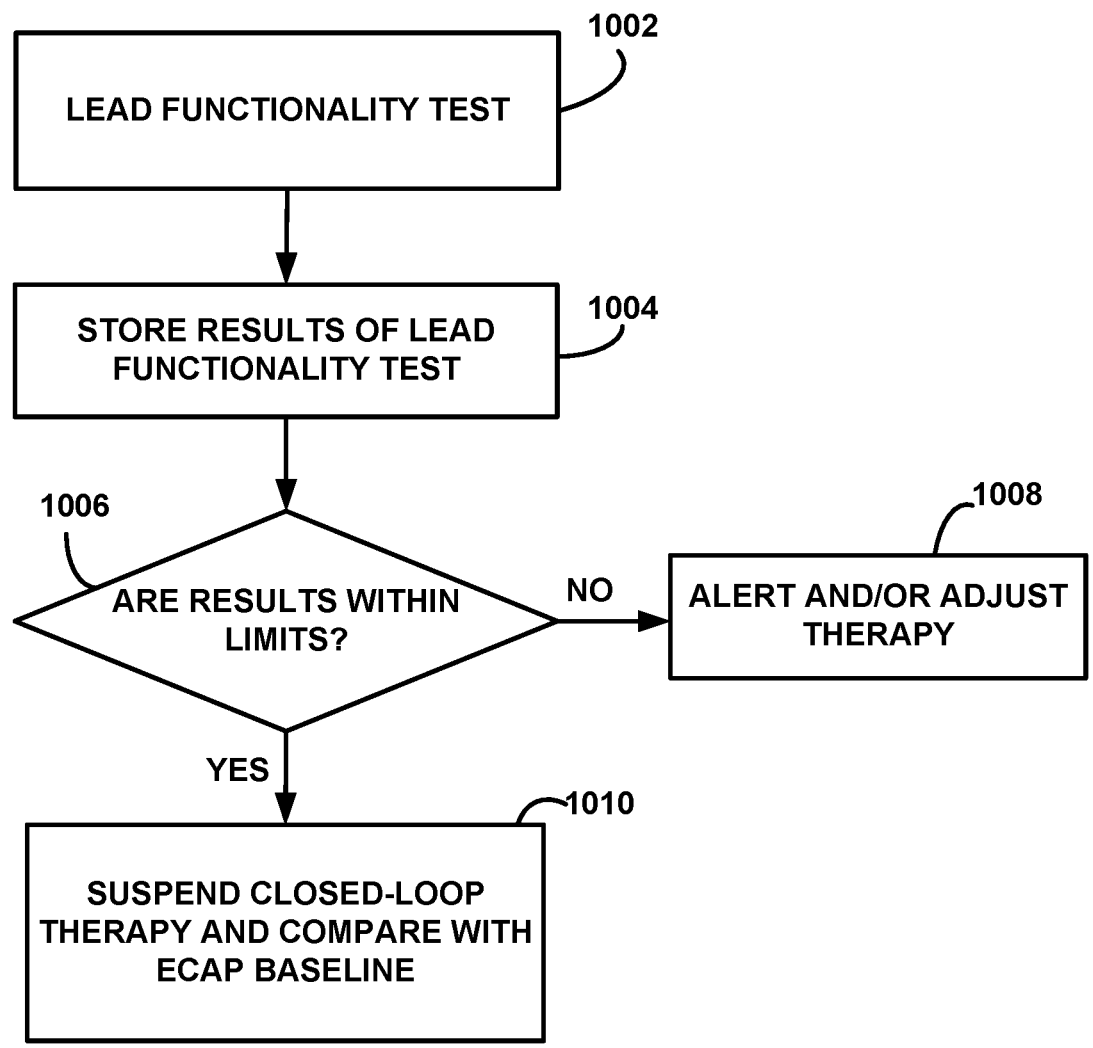
FIG. 10 is a flow diagram illustrating an example method for automatically performing lead integrity testing according to examples of the present disclosure.

FIG. 10 is a flow diagram illustrating an example method for automatically performing lead integrity testing according to examples of the present disclosure. For example, the described method may be used by IMD 200 in FIG. 2 to automatically perform lead integrity testing.

IMD 200 performs lead integrity testing (1002). Lead functionality closed-looping, e.g., lead impedance or current closed-looping, may be performed using any known techniques. For example, to perform lead integrity testing, IMD 200 may deliver a non-therapeutic pulse via a combination of two electrodes, measure final voltage or current amplitude for the pulse, and determine an impedance for the combination based on the measured final amplitude. Testing may be repeated for a plurality of electrode combinations and/or for the same combinations of electrodes on multiple occasions according to the instructions stored by IMD 200.

After performing the lead integrity test, IMD 200 stores the results of the test in storage device 212 (1004). IMD 200 may also determine if the lead integrity test results are within limits defined by the stored instructions (1006). IMD 200 may compare measured impedance or current values for one or more combinations, or one or more averages determined based on such values, to one or more threshold values stored in storage device 212 of IMD 200. Further, IMD 200 may compare a rate of change for an average impedance or current value to one or more threshold values stored in storage device 212 of IMD 200. In some embodiments, IMD 200 may maintain multiple average values calculated over longer and shorter periods of time in storage device 212 for comparison to multiple thresholds. A shorter period average that exceeds a threshold, for example, may indicate a more severe problem that requires immediate attention, such as a lead fracture.

If one or more of the test results are outside limits defined by the instructions, thresholds or other information stored in the IMD memory, IMD 200 may adjust patient therapy, store an alert that the patient or a clinician may receive the next time a programmer communicates with IMD 200, cause external programmer 300 to immediately alert patient 105, or directly provide some other audible, vibratory, or stimulation alert to the patient, e.g., via IMD 200 (1008). For example, if an electrode conductor has a fracture, IMD 200 may stop delivering therapies that use that electrode. If an electrode has been surrounded by fibrous or other tissue growth, which may cause an increase in the measured or average impedances associated with that electrode, the ID may increase the voltage or current amplitude for therapies that use that electrode.

If no lead integrity issue was discovered, then diagnostic program 216 suspends closed-loop therapy program 214 and begins a periodic comparison with an ECAP signal baseline characteristic value until an ECAP signal characteristic value is found ("YES" branch of block 1006) (1010). Once the ECAP signal characteristic values are found to be within a tolerance of the ECAP signal baseline characteristic value, closed-loop therapy 214 may resume.

This disclosure includes various examples, such as the following examples.

Example 1A: A method comprising: receiving, by processing circuitry, information indicative of one or more evoked compound action potential (ECAP) signals, the one or more ECAP signals sensed by at least one electrode carried by a medical lead; determining, by processing circuitry, that at least one characteristic value of the one or more ECAP signals is outside of an expected range; and responsive to determining that the at least one characteristic value of the one or more ECAP signals is outside of the expected range, performing, by the processing circuitry, a lead integrity test for the medical lead.

Example 2A: The method of example 1A, further comprising: receiving, by the processing circuitry, accelerometer data indicative of patient movement; determining, by the processing circuitry and based on the accelerometer data, that a circadian rhythm of a patient is within a normal circadian rhythm range; determining, by the processing circuitry, the at least one characteristic value of the one or more ECAP signals is below the expected range; and responsive to determining that the circadian rhythm is within the normal circadian rhythm range and the characteristic value of the one or more ECAP signals is below the expected range, performing the lead integrity test.

Example 3A. The method of example 2A, further comprising performing the lead integrity test that comprises measuring an impedance for the at least one electrode carried by the medical lead and determining whether the measured impedance is within one or more thresholds defined by stored instructions.

Example 4A. The method of any of examples 1A through 3A, further comprising: determining, by the processing circuitry, that the at least one characteristic value of the one or more ECAP signals is an amplitude above the expected range; comparing, by the processing circuitry, the at least one characteristic value of the one or more ECAP signals to at least one characteristic value of a baseline ECAP signal; and determining, by the processing circuitry, based on the comparison, that the at least one characteristic value of the one or more ECAP signals is outside of an expected range of the at least one characteristic value of the baseline ECAP signal.

Example 5A. The method of example 4A, further comprising: responsive to a determination the at least one characteristic value is outside the expected range from the at least one characteristic value of the baseline ECAP signal, performing a lead integrity test that comprises measuring an impedance for the at least one electrode carried by the medical lead; determining, by the processing circuitry and based on lead integrity test results, that the measured impedance of the at least one electrode is within one or more thresholds defined by stored instructions; and outputting, by the processing circuitry based on a successful lead integrity test, a request for a user to adjust a closed-loop stimulation algorithm that controls delivery of electrical stimulation based on the ECAP signals.

Example 6A. The method of example 4A, further comprising: responsive to determining that the at least one characteristic value of the one or more ECAP signals is outside the expected range of the at least one characteristic value of the baseline ECAP signal, performing the lead integrity test; determining, by the processor and based on the lead integrity test, that impedance measured at the at least one electrode of the medical lead is outside one or more thresholds defined by stored instructions; and responsive to the at least one electrode of the medical lead failing the lead integrity test, requesting, by the processing circuitry, a user to adjust a closed-loop stimulation algorithm that controls delivery of electrical stimulation based on the ECAP signals.

Example 7A. The method of example 4A, further comprising: responsive to the comparison that the at least one characteristic value is outside the threshold of the at least one characteristic value of the baseline ECAP signal, determining, by the processing circuitry, the at least one characteristic value of the one or more ECAP signals comprises noise; performing the lead integrity test for the at least one electrode carried by the medical lead; determining, by the processing circuitry and based on the lead integrity test, the at least one electrode is within one or more thresholds defined by stored instructions; responsive to the lead integrity test, suspending, by the processing circuitry, closed-loop stimulation;

periodically comparing, by the processing circuitry, the at least one characteristic value of the one or more ECAP signals against at least one characteristic value of the baseline ECAP signal; and responsive to the comparison of the at least one characteristic value of the one or more ECAP signals being within the expected range of the at least one characteristic value of the baseline ECAP signals, resuming, by the processing circuitry, the closed-loop stimulation.

Example 8A. The method of example 4A, wherein the at least one electrode comprises a first recording electrode combination, and wherein the method further comprises: responsive to the comparison that the at least one characteristic value is outside the expected range from the at least one characteristic value of the baseline ECAP signal, determining, by the processing circuitry, the at least one characteristic value of the one or more ECAP signals comprises noise; performing the lead integrity test for the at least one electrode carried by the medical lead; responsive to lead integrity test, determining, by the processing circuitry, the lead integrity test of the first recording electrode combination is not within one or more thresholds defined by stored instructions; and responsive to the determination the first recording electrode combination is not within the one or more thresholds defined by the stored instructions, selecting, by the processing circuitry, a second recording electrode combination.

Example 9A. The method of any of examples 1A through 8A, further comprising: determining, by the processing circuitry, over a period of time the characteristic value of the one or more ECAP signals is a variance of the one or more ECAP signals; and responsive to the determination of the variance between the characteristic value and the one or more ECAP signals, periodically comparing, by the processing circuitry, the at least one characteristic value of the one or more ECAP signals against the at least one characteristic value of the baseline ECAP signal.

Example 10A. The method of example 9A, further comprising: responsive to a comparison of the at least one characteristic value of the one or more ECAP signals being outside the expected range of the at least one characteristic value of the baseline ECAP signals, performing the lead integrity test for the at least one electrode carried by the medical lead; determining, by the processing circuitry, the lead integrity test is within limits defined by stored instructions; suspending, by the processing circuitry, closed-loop stimulation; periodically comparing, by the processing circuitry, the at least one characteristic value of the one or more ECAP signals against at least one characteristic value of the baseline ECAP signal; and resuming, by the processing circuitry and based upon the at least one characteristic value of the one or more ECAP signals within the expected range of the at least one characteristic value of the baseline ECAP signal, closed-loop stimulation.

Example 1B. A medical device comprising: stimulation generation circuitry configured to deliver a first stimulation pulse to a patient; sensing circuitry configured to sense information indicative of one or more evoked compound action potential (ECAP) signals, where the sensing circuitry comprises at least one electrode carried by a medical lead; and processing circuitry configured to: receive information indicative of the one or more ECAP signals sensed by the at least one electrode carried by the medical lead; determine that at least one characteristic value of the one or more ECAP signals is outside of an expected range; and responsive to determining that the at least one characteristic value of the one or more ECAP signals is outside of the expected range, perform a lead integrity test for the medical lead.

Example 2B. The medical device of example 1B, wherein the processing circuitry is further configured to: receive accelerometer data indicative of patient movement; determine, based on the accelerometer data, that a circadian rhythm of a patient is within a normal circadian rhythm range; determine the at least one characteristic value of the one or more ECAP signals is below the expected range; and responsive to determining that the circadian rhythm is within the normal circadian rhythm range and the characteristic value of the one or more ECAP signals is below the expected range, performing the lead integrity test.

Example 3B. The medical device of example 2B, wherein the lead integrity test comprises measuring an impedance for the at least one electrode carried by the medical lead and determining whether the measured impedance is within limits defined by stored instructions.

Example 4B. The medical device of any of examples 1B through 3B, wherein the medical device comprises an implantable medical device comprising the stimulation generation circuitry, the sensing circuitry, and the processing circuitry.

Example 5B. The medical device of any of examples 1B through 4B, wherein the processing circuitry is further configured to: determine that the at least one characteristic value of the one or more ECAP signals is an amplitude above the expected range; compare the at least one characteristic value of the one or more ECAP signals to the at least one characteristic value of a baseline ECAP signal; and determine, based on the comparison, that the at least one characteristic value is outside an expected range of the at least one characteristic value of the baseline ECAP signal.

Example 6B. The medical device of example 5B, wherein the processing circuitry is further configured to: perform, based on a determination the at least one characteristic value is outside the expected range from the at least one characteristic value of the baseline ECAP signal, the lead integrity test that comprises measuring an impedance for the at least one electrode carried by the medical lead and determining whether the measured impedance is within limits defined by stored instructions; determine, based on the lead integrity test results, that the medical lead measured impedance is within the limits defined by the stored instructions; and output a request for a user to adjust a closed-loop stimulation algorithm that controls delivery of electrical stimulation based on the ECAP signals responsive.

Example 7B. The medical device of example 5B, wherein the processing circuitry is further configured to: perform, based on determining that the at least one characteristic value is outside the expected range from the at least one characteristic value of the baseline ECAP signal, the lead integrity test that comprises measuring an impedance for the at least one electrode carried by the medical lead; determine, based on the lead integrity test results, that the at least one electrode of the medical lead failed the lead integrity test; and request a user to adjust a closed-loop stimulation algorithm that controls delivery of electrical stimulation based on the ECAP signals.

Example 8B. The medical device of example 5B, wherein the processing circuitry is further configured to: determine, based on the comparison that the at least one characteristic value is outside the expected range of the at least one characteristic value of the baseline ECAP signal, the at least one characteristic value of the one or more ECAP signals comprises noise; perform the lead integrity test for the at least one electrode carried by the medical lead; determine, based on the lead integrity test, the at least one electrode is within one or more thresholds defined by stored instructions; suspend, based on the lead integrity test, closed-loop stimulation; periodically compare the at least one characteristic value of the one or more ECAP signals against at least one characteristic value of the baseline ECAP signal; and resume, based on the comparison of the at least one characteristic value of the one or more ECAP signals being within the expected range of the at least one characteristic value of the baseline ECAP signals, the closed-loop stimulation.

Example 9B. The medical device of example 5B, wherein the at least one electrode comprises at least one recording electrode, and wherein the processing circuitry is further configured to: determine, based on the comparison that the at least one characteristic value is outside the expected range from the at least one characteristic value of the baseline ECAP signal, the at least one characteristic value of the one or more ECAP signals comprises noise; perform the lead integrity test for the at least one electrode carried by the medical lead; determine, based on the lead integrity test, the first recording electrode combination is not within one or more thresholds defined by stored instructions; and select, based on the determination the first recording electrode combination is not within the one or more thresholds defined by the stored instructions, a second recording electrode combination.

Example 1C. A computer-readable storage medium comprising instructions that, when executed, cause processing circuitry to: receive information indicative of one or more evoked compound action potential (ECAP) signals, the one or more ECAP signals sensed by at least one electrode carried by a medical lead; determine that at least one characteristic value of the one or more ECAP signals is outside of an expected range; and perform, based on the determination that the at least one characteristic value of the one or more ECAP signals is outside of the expected range, a lead integrity test for the medical lead.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units may be intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A method comprising:
   receiving, by processing circuitry, information indicative of one or more evoked compound action potential (ECAP) signals, the one or more ECAP signals sensed by at least one electrode carried by a medical lead;
   receiving, by the processing circuitry, accelerometer data indicative of patient movement;
   determining, by the processing circuitry and based on the accelerometer data, that at least one characteristic value of the one or more ECAP signals is outside of an expected range; and
   responsive to determining that the at least one characteristic value of the one or more ECAP signals is outside of the expected range, performing, by the processing circuitry, an action.

2. The method of claim 1, further comprising:
   determining, by the processing circuitry and based on the accelerometer data, that a circadian rhythm of a patient is within a normal circadian rhythm range;
   determining, by the processing circuitry, the at least one characteristic value of the one or more ECAP signals is below the expected range; and
   responsive to determining that the circadian rhythm is within the normal circadian rhythm range and the characteristic value of the one or more ECAP signals is below the expected range, performing the action.

3. The method of claim 2, wherein the action comprises a lead integrity test, and wherein performing the lead integrity test further comprises performing the lead integrity test by at least measuring an impedance for the at least one electrode carried by the medical lead and determining whether the measured impedance is within one or more thresholds defined by stored instructions.

4. The method of claim 1, further comprising:
   determining, by the processing circuitry, that the at least one characteristic value of the one or more ECAP signals is an amplitude above the expected range;
   comparing, by the processing circuitry, the at least one characteristic value of the one or more ECAP signals to at least one characteristic value of a baseline ECAP signal; and
   determining, by the processing circuitry, based on the comparison, that the at least one characteristic value of the one or more ECAP signals is outside of an expected range of the at least one characteristic value of the baseline ECAP signal.

5. The method of claim 4, further comprising:
   responsive to a determination the at least one characteristic value is outside the expected range from the at least one characteristic value of the baseline ECAP signal, performing, as the action, a lead integrity test that comprises measuring an impedance for the at least one electrode carried by the medical lead;
   determining, by the processing circuitry and based on lead integrity test results, that the measured impedance of the at least one electrode is within one or more thresholds defined by stored instructions; and
   outputting, by the processing circuitry based on a successful lead integrity test, a request for a user to adjust a closed-loop stimulation algorithm that controls delivery of electrical stimulation based on the ECAP signals.

6. The method of claim 4, further comprising:
   responsive to determining that the at least one characteristic value of the one or more ECAP signals is outside the expected range of the at least one characteristic value of the baseline ECAP signal, performing, as the action, a lead integrity test;

determining, by the processor and based on the lead integrity test, that impedance measured at the at least one electrode of the medical lead is outside one or more thresholds defined by stored instructions; and responsive to the at least one electrode of the medical lead failing the lead integrity test, requesting, by the processing circuitry, a user to adjust a closed-loop stimulation algorithm that controls delivery of electrical stimulation based on the ECAP signals.

7. The method of claim 1, further comprising:

determining, by the processing circuitry, over a period of time the characteristic value of the one or more ECAP signals is a variance of the one or more ECAP signals; and responsive to the determination of the variance between the characteristic value and the one or more ECAP signals, periodically comparing, by the processing circuitry, the at least one characteristic value of the one or more ECAP signals against the at least one characteristic value of the baseline ECAP signal.

8. The method of claim 7, further comprising:

responsive to a comparison of the at least one characteristic value of the one or more ECAP signals being outside the expected range of the at least one characteristic value of the baseline ECAP signals, performing a lead integrity test as the action for the at least one electrode carried by the medical lead;

determining, by the processing circuitry, the lead integrity test is within limits defined by stored instructions;

suspending, by the processing circuitry, closed-loop stimulation;

periodically comparing, by the processing circuitry, the at least one characteristic value of the one or more ECAP signals against at least one characteristic value of the baseline ECAP signal; and resuming, by the processing circuitry and based upon the at least one characteristic value of the one or more ECAP signals within the expected range of the at least one characteristic value of the baseline ECAP signal, closed-loop stimulation.

9. The method of claim 1, wherein performing the action comprises suspending closed-loop adjustment of one or more parameters that define electrical stimulation therapy delivered to a patient.

10. The method of claim 1, wherein performing the action comprises reconfiguring at least one of a stimulation electrode combination or a sensing electrode combination.

11. A medical device comprising:

stimulation generation circuitry configured to deliver a first stimulation pulse to a patient;

sensing circuitry configured to sense information indicative of one or more evoked compound action potential (ECAP) signals, where the sensing circuitry comprises at least one electrode carried by a medical lead; and processing circuitry configured to:

receive information indicative of the one or more ECAP signals sensed by the at least one electrode carried by the medical lead;

receive accelerometer data indicative of patient movement;

determine, based on the accelerometer data, that at least one characteristic value of the one or more ECAP signals is outside of an expected range; and responsive to determining that the at least one characteristic value of the one or more ECAP signals is outside of the expected range, perform an action.

12. The medical device of claim 11, wherein the processing circuitry is further configured to:

determine, based on the accelerometer data, that a circadian rhythm of a patient is within a normal circadian rhythm range;

determine the at least one characteristic value of the one or more ECAP signals is below the expected range; and responsive to determining that the circadian rhythm is within the normal circadian rhythm range and the characteristic value of the one or more ECAP signals is below the expected range, performing the action.

13. The medical device of claim 12, wherein the action comprises a lead integrity test, and wherein performing the processing circuitry is configured to perform the lead integrity test by at least measuring an impedance for the at least one electrode carried by the medical lead and determining whether the measured impedance is within limits defined by stored instructions.

14. The medical device of claim 11, wherein the medical device comprises an implantable medical device comprising the stimulation generation circuitry, the sensing circuitry, and the processing circuitry.

15. The medical device of claim 11, wherein the processing circuitry is further configured to:

determine that the at least one characteristic value of the one or more ECAP signals is an amplitude above the expected range;

compare the at least one characteristic value of the one or more ECAP signals to the at least one characteristic value of a baseline ECAP signal; and determine, based on the comparison, that the at least one characteristic value is outside an expected range of the at least one characteristic value of the baseline ECAP signal.

16. The medical device of claim 15, wherein the processing circuitry is further configured to:

perform, based on a determination the at least one characteristic value is outside the expected range from the at least one characteristic value of the baseline ECAP signal, a lead integrity test, as the action, that comprises measuring an impedance for the at least one electrode carried by the medical lead and determining whether the measured impedance is within limits defined by stored instructions;

determine, based on the lead integrity test results, that the medical lead measured impedance is within the limits defined by the stored instructions; and output a request for a user to adjust a closed-loop stimulation algorithm that controls delivery of electrical stimulation based on the ECAP signals responsive.

17. The medical device of claim 15, wherein the processing circuitry is further configured to:

perform, based on determining that the at least one characteristic value is outside the expected range from the at least one characteristic value of the baseline ECAP signal, a lead integrity test, as the action, that comprises measuring an impedance for the at least one electrode carried by the medical lead;

determine, based on the lead integrity test results, that the at least one electrode of the medical lead failed the lead integrity test; and request a user to adjust a closed-loop stimulation algorithm that controls delivery of electrical stimulation based on the ECAP signals.

18. The medical device of claim 11, wherein the processing circuitry is configured to perform the action by at least suspending closed-loop adjustment of one or more parameters that define electrical stimulation therapy delivered to a patient.

19. The medical device of claim 11, wherein the processing circuitry is configured to perform the action by at least reconfiguring at least one of a stimulation electrode combination or a sensing electrode combination.

20. A computer-readable storage medium comprising instructions that, when executed, cause processing circuitry to:
- receive information indicative of one or more evoked compound action potential (ECAP) signals, the one or more ECAP signals sensed by at least one electrode carried by a medical lead;
- determine that at least one characteristic value of the one or more ECAP signals is outside of an expected range;
- receive accelerometer data indicative of patient movement;
- determine, based on the accelerometer data, that a circadian rhythm of a patient is within a normal circadian rhythm range; and
- responsive to determining that the circadian rhythm is within the normal circadian rhythm range and the characteristic value of the one or more ECAP signals is outside of the expected range, perform an action.

* * * * *